US011969300B2

(12) United States Patent
McFall et al.

(10) Patent No.: US 11,969,300 B2
(45) Date of Patent: Apr. 30, 2024

(54) IMPLANTABLE MEDICAL LEAD INDICATORS

(71) Applicant: Medtronic, Inc., Minneapolis, MN (US)

(72) Inventors: George W. McFall, Minneapolis, MN (US); Thomas D. Brostrom, Wayzata, MN (US); Mark T. Marshall, Cape Coral, FL (US); Dina L. Williams, Andover, MN (US); Megan Harris, Andover, MN (US); Keith D. Anderson, Minneapolis, MN (US); Maggie J. Pistella, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 70 days.

(21) Appl. No.: 17/400,824

(22) Filed: Aug. 12, 2021

(65) Prior Publication Data

US 2021/0369386 A1    Dec. 2, 2021

Related U.S. Application Data

(62) Division of application No. 16/021,287, filed on Jun. 28, 2018, now Pat. No. 11,096,757.

(51) Int. Cl.
*A61N 1/39* (2006.01)
*A61B 5/25* (2021.01)
(Continued)

(52) U.S. Cl.
CPC .......... *A61B 90/08* (2016.02); *A61B 17/3468* (2013.01); *A61B 2090/0807* (2016.02); *A61B 2560/066* (2013.01); *A61N 1/3956* (2013.01)

(58) Field of Classification Search
CPC .......... A61N 1/04; A61N 1/05; A61N 1/0502; A61N 1/0504; A61N 1/3956; A61B 90/08;
(Continued)

(56) References Cited

U.S. PATENT DOCUMENTS 5,084,022 A   1/1992   Claude
5,411,528 A   5/1995   Miller et al.
(Continued)

OTHER PUBLICATIONS

International Search Report and Written Opinion of International Application No. PCT/US2019/038894, dated Oct. 15, 2019, 10 pp.
(Continued)

*Primary Examiner* — Adam Z Minchella
(74) *Attorney, Agent, or Firm* — Shumaker & Sieffert, P.A.

(57) ABSTRACT

An implantable medical lead may include an electrode at a distal portion of the lead that is configured to monitor or provide therapy to a target site. The lead may include a visible indicator that is visible to the naked eye of a clinician at a medial portion of the lead that is configured to indicate when the electrodes of the lead are longitudinally and radially aligned properly to monitor or treat the target site. A clinician may insert the lead into the patient using an introducer sheath inserted to a predetermined depth into the patient and subsequently aligning the distal portion of the lead by orienting the indicator at an entry port of the introducer sheath.

18 Claims, 14 Drawing Sheets

(51) Int. Cl.
*A61B 17/34* (2006.01)
*A61B 90/00* (2016.01)

(58) Field of Classification Search
CPC ........ A61B 17/3468; A61B 2090/0807; A61B 2560/066
See application file for complete search history.

(56) References Cited

U.S. PATENT DOCUMENTS

| | | | |
|---|---|---|---|
| 6,428,512 | B1 | 8/2002 | Anderson et al. |
| 7,251,532 | B2 | 7/2007 | Hess et al. |
| 7,499,755 | B2* | 3/2009 | Cross, Jr. .............. A61N 1/0553 |
| | | | 607/117 |
| 8,204,569 | B2 | 6/2012 | Gerber et al. |
| 10,293,164 | B2* | 5/2019 | Nash .................... A61N 1/3611 |
| 10,398,890 | B2 | 9/2019 | Gerber et al. |
| 2002/0165536 | A1* | 11/2002 | Kelley ..................... A61N 1/05 |
| | | | 606/41 |
| 2005/0171587 | A1 | 8/2005 | Daglow et al. |
| 2007/0050005 | A1* | 3/2007 | Lauro ................ H01R 13/5804 |
| | | | 607/126 |
| 2008/0103569 | A1* | 5/2008 | Gerber ................ A61N 1/0534 |
| | | | 607/115 |
| 2010/0030312 | A1 | 2/2010 | Shen |
| 2011/0190786 | A1* | 8/2011 | Gerber ................... A61B 17/00 |
| | | | 607/116 |
| 2013/0131768 | A1 | 5/2013 | Possover |
| 2014/0094823 | A1 | 4/2014 | Carcieri et al. |
| 2014/0255298 | A1 | 9/2014 | Cole et al. |
| 2014/0330287 | A1 | 11/2014 | Thompson-Nauman et al. |
| 2015/0374957 | A1 | 12/2015 | Minar et al. |
| 2016/0158567 | A1* | 6/2016 | Marshall .............. A61N 1/0504 |
| | | | 607/116 |
| 2017/0021139 | A1 | 1/2017 | Bajema et al. |
| 2017/0065401 | A1* | 3/2017 | Fearnot .................... A61F 2/07 |
| 2017/0095657 | A1 | 4/2017 | Reddy et al. |
| 2017/0157399 | A1 | 6/2017 | Anderson et al. |
| 2017/0157412 | A1 | 6/2017 | Nikolski et al. |
| 2017/0157413 | A1 | 6/2017 | Anderson et al. |
| 2017/0157414 | A1 | 6/2017 | Anderson et al. |
| 2017/0266442 | A1 | 9/2017 | Jackson |
| 2017/0312494 | A1 | 11/2017 | Seifert et al. |
| 2019/0344071 | A1 | 11/2019 | Williams et al. |
| 2020/0000542 | A1 | 1/2020 | McFall et al. |

OTHER PUBLICATIONS

International Preliminary Report on Patentability from International Application No. PCT/US2019/038894, dated Dec. 29, 2020, 5 pp.
Prosecution History from U.S. Appl. No. 16/021,287, dated Apr. 13, 2020 through Apr. 28, 2021, 81 pp.

* cited by examiner

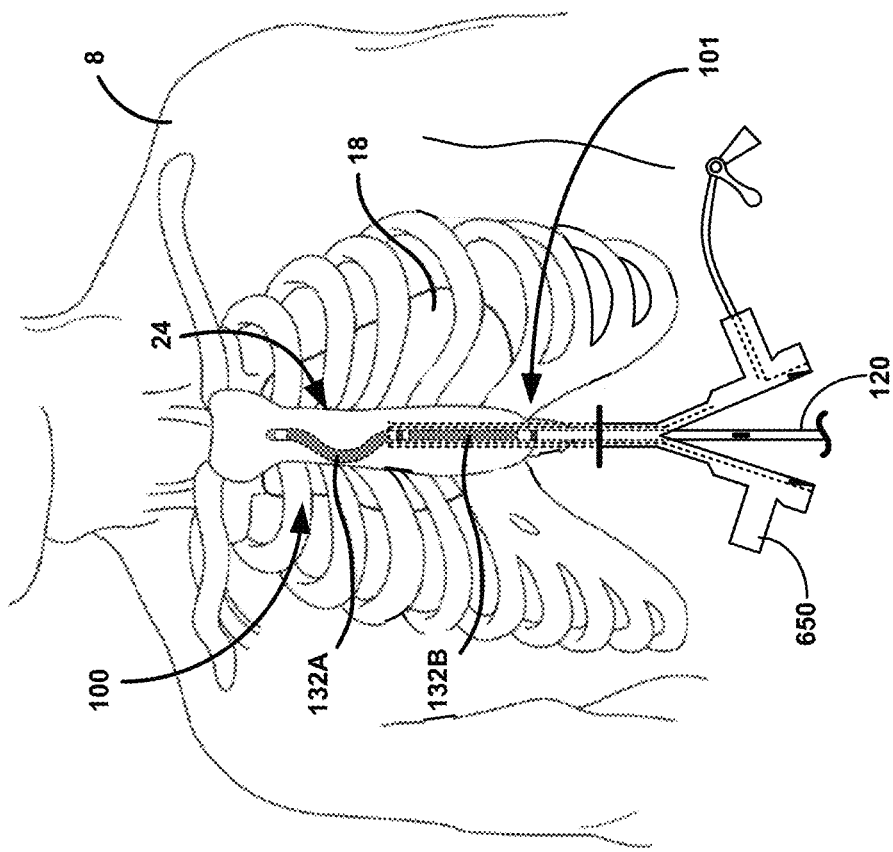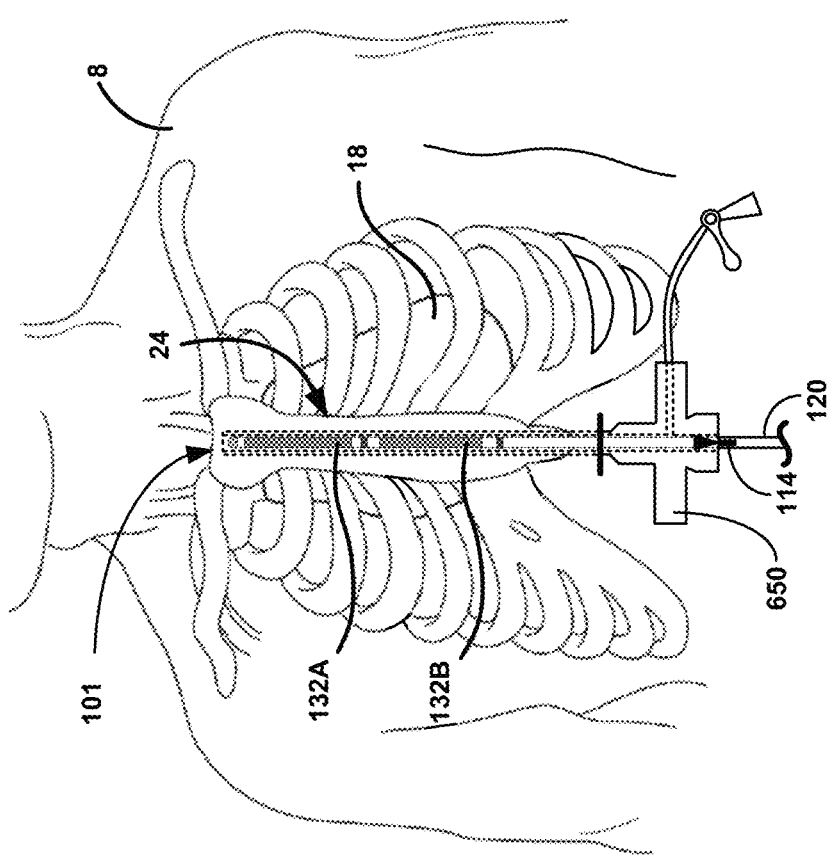

IMPLANTABLE MEDICAL LEAD INDICATORS

This application is a divisional of U.S. patent application Ser. No. 16/021,287, filed Jun. 28, 2018, the entire content of which is incorporated by reference herein.

TECHNICAL FIELD

The disclosure generally relates to implantable and/or insertable medical leads.

BACKGROUND

Medical operations may include navigating an insertable or implantable medical lead to a specific target site within a human patient. For example, a distal portion of the insertable or implantable medical lead may include one or more electrodes configured to monitor a parameter of target site of the patient or provide therapy to the target site of the patient. In some examples, the target site may not be directly accessible, such that a delivery system may have to navigate a portion of the patient's body before the distal portion of the insertable or implantable medical lead arrives at the target site.

SUMMARY

Aspects of the disclosure are directed to a medical device system that includes an implantable medical lead. The implantable medical lead includes a distal portion, a proximal portion, a visible indicator located at a discrete longitudinal position and a discrete radial position on the implantable medical lead between the distal portion and the proximal portion, and one or more electrodes on the distal portion configured to at least one of deliver electrical stimulation or sense electrical signals of a patient when implanted within the patient at a target site. The medical device system also includes an introducer sheath including a distal portion configured to be inserted into the patient to a predetermined depth and an entry port at a proximal portion of the introducer sheath. The distal portion of the implantable medical lead is configured to be inserted into the entry port of the introducer sheath and moved towards the distal portion of the introducer sheath. The visible indicator is configured to indicate a radial orientation and longitudinal depth of the distal portion of the lead within the introducer sheath.

Other aspects of the disclosure are directed to a method of inserting an implantable medical lead that includes inserting an exit port of an introducer sheath a predetermined depth into a patient. The introducer sheath includes an entry port at a proximal portion of the introducer sheath. The method also includes inserting a distal portion of the implantable medical lead into the entry port of the introducer sheath. The distal portion includes one or more electrodes configured to at least one of deliver electrical stimulation or sense electrical signals of a patient when implanted within the patient at a target site. The implantable medical lead includes a visible indicator located at a discrete longitudinal position and a discrete radial position on the implantable medical lead between the distal portion and a proximal portion of the implantable medical lead. The method also includes orienting the distal portion of the implantable medical lead at the target site by aligning the visible indicator at the entry port of the introducer sheath.

Other aspects of the disclosure are directed to an implantable medical lead that includes a distal portion that defines a serpentine shape and extends proximally from a distal tip of the implantable medical lead. The implantable medical lead also includes a proximal portion configured to be coupled to an implantable medical device. The implantable medical lead also includes a visible indicator located between the distal portion and the proximal portion at a discrete radial position and a discrete longitudinal position between 18 and 25 centimeters from the distal tip along a longitudinal axis of the implantable medical lead. The visible indicator is configured to indicate a radial orientation of the distal portion of the implantable medical lead within an introducer sheath and indicate a depth of the distal portion of the implantable medical lead within the introducer sheath. The implantable medical lead also includes a first pacing and/or sensing electrode that defines a proximal edge between 10 and 12 centimeters distal of the visible indicator along the longitudinal axis. The implantable medical lead also includes a first defibrillation electrode that defines a proximal edge between 11 and 13 centimeters distal of the visible indicator along the longitudinal axis and is configured to curve toward a right side of a heart of a patient upon implantation. The implantable medical lead also includes a second pacing and/or sensing electrode that defines a proximal edge between 14.5 and 16.5 centimeters distal of the visible indicator along the longitudinal axis. The implantable medical lead also includes a second defibrillation electrode that defines a proximal edge between 15 and 17 centimeters distal of the visible indicator along the longitudinal axis and is configured to curve toward the right side of the heart of the patient upon implantation. The implantable medical lead also includes an anchoring portion that extends proximally between 9 and 12 centimeters from a distal end of the anchoring portion that is between 1 and 2 centimeters distal of the first pacing and/or sensing electrode. An outer surface of the anchoring portion defines an interlocking interface. The implantable medical lead also includes an anchoring sleeve that is slideable over the anchoring portion and is configured to interlock with the interlocking interface in response to the anchoring sleeve being anchored to the patient.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

FIGS. 11A and 11B are conceptual and schematic diagrams illustrating perspective views of the lead of FIG. 2A and introducer sheath of FIG. 10A inserted in a substernal space and the introducer sheath being split as it is retracted from the substernal space.

DETAILED DESCRIPTION

Aspects of this disclosure relate to methods and systems for delivering an insertable or implantable medical lead for an implantable medical device (hereinafter referred to as "IMD") to a target site in a patient. The target site may include many locations within a patient, though for purposes of clarity this disclosure predominantly discusses target sites adjacent a heart of the patient. The medical lead may include electrodes at a distal portion of the lead that are configured to monitor electrical signals of the patient and/or deliver electrical stimulation therapy to the target site. The lead may further include a proximal portion with such components as a hub for the lead. The lead may include a visible indicator (e.g., a physical feature that is visible to the naked eye of a clinician) between the proximal portion and the distal portion of the lead. The visible indicator may be configured to indicate when the distal portion of the lead is longitudinally and radially aligned properly with respect to the target site when inserted into the patient with an introducer sheath. For example, a clinician may insert the lead into the patient using the introducer sheath, wherein the introducer sheath is inserted to a predetermined depth into the patient. One or more markings on the introducer sheath may indicate when the introducer sheath is inserted to the predetermined depth.

The clinician may align the distal portion of the lead by aligning the visible indicator with an orientation region of the introducer sheath. An orientation region may include one or more visible markers on an outside of the introducer sheath, and/or the orientation region may include a predetermined portion of the introducer sheath that is configured to face the clinician when the introducer sheath is inserted into a patient. In this manner a clinician may properly align the distal portion of the lead despite the distal portion being hidden or otherwise not visible by the naked eye to the clinician during the implant procedure. By promoting the proper alignment/orientation of the distal portion of the lead, both an efficacy of a system that employs the lead as well as the efficacy of the implant procedure may be improved. Further, use of the lead may reduce radiation exposure of the patient by enabling a clinician to visually align the distal end of a lead without the use of or with reduced use of fluoroscopy or other imaging to align or orient the distal portion of the lead.

Figure 1A:
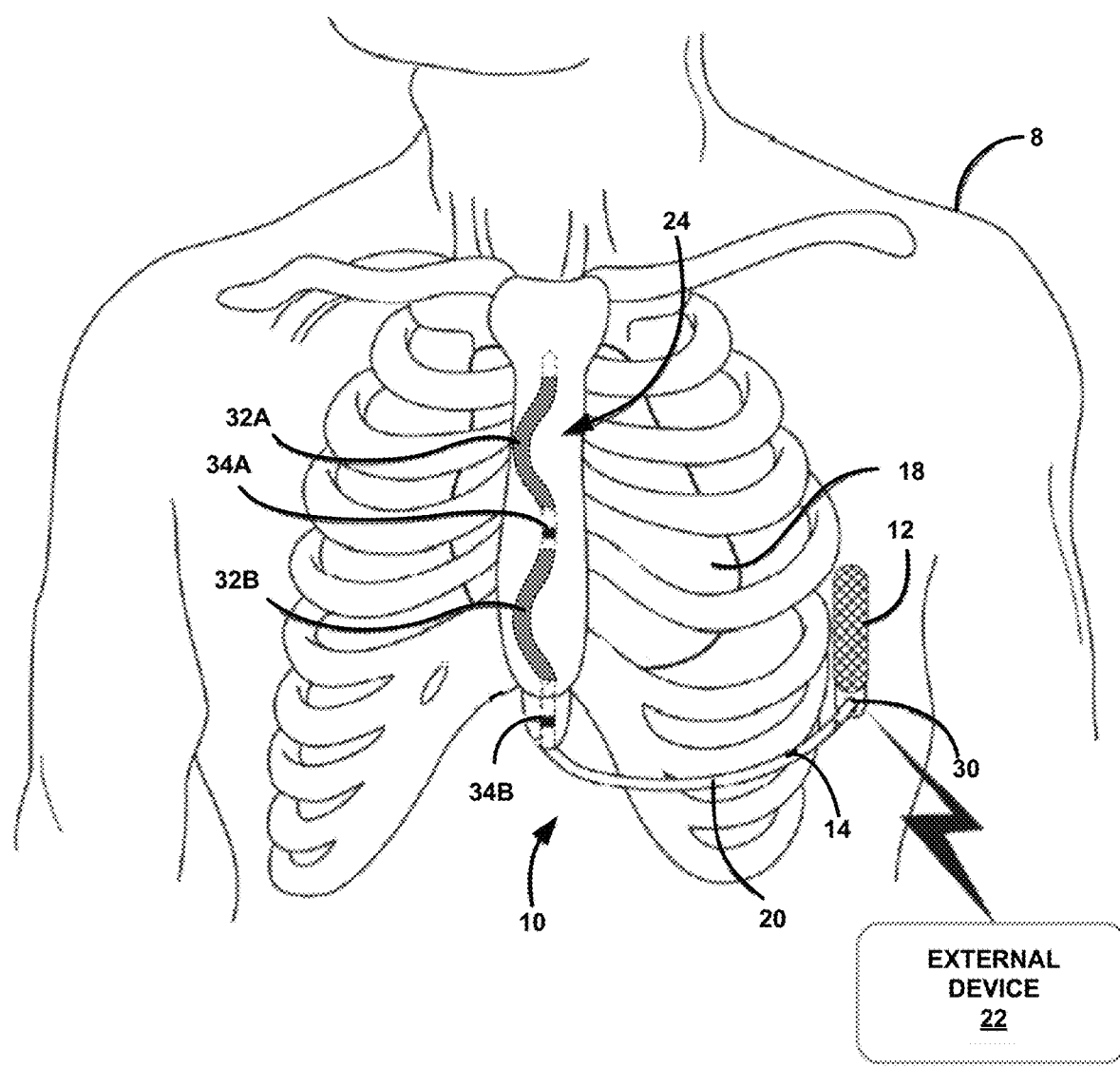
FIGS. 1A-1C are front-view, side-view, and top-view conceptual drawings, respectively, illustrating an example medical device system in conjunction with a patient.
Figure 1B:
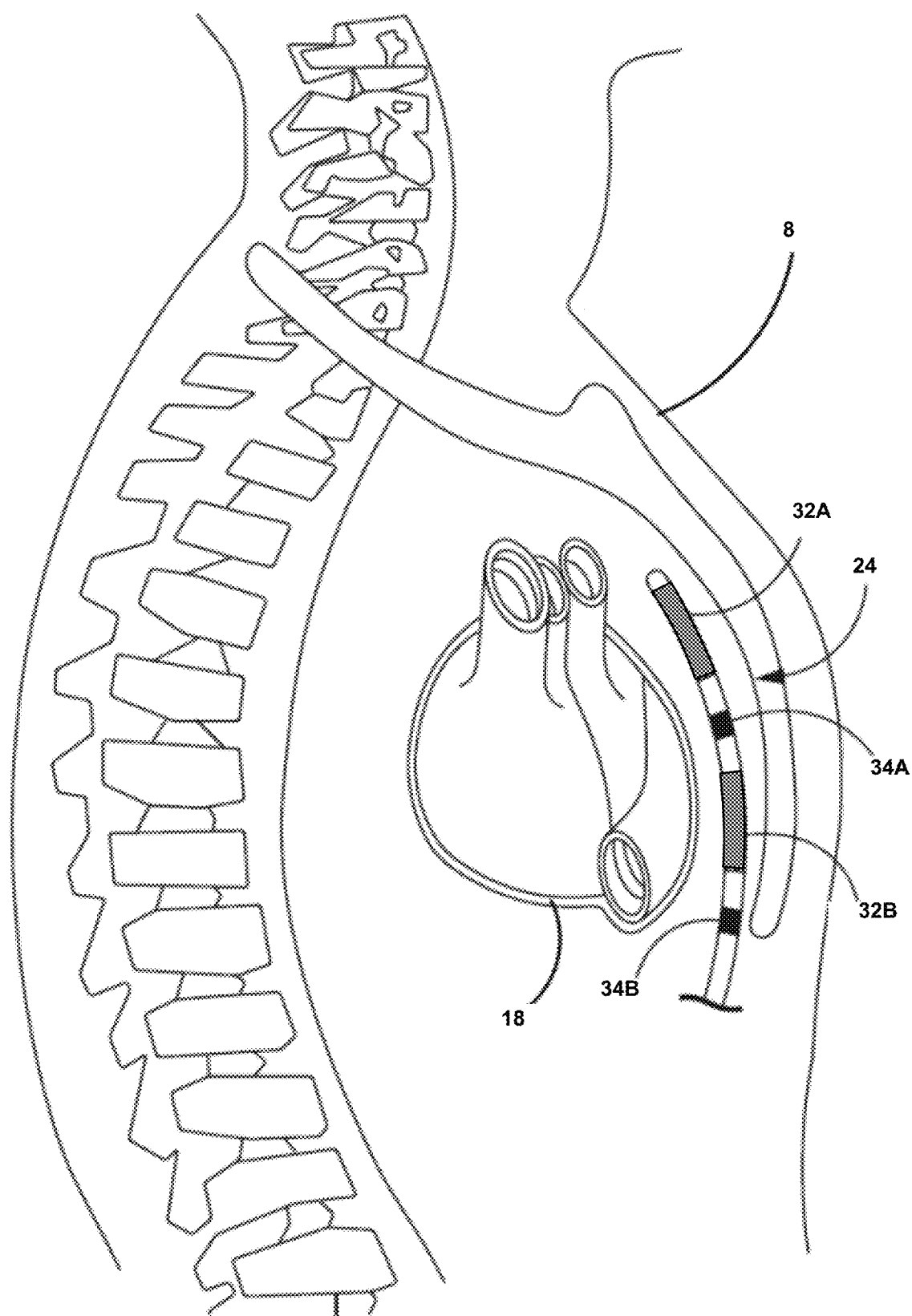
Figure 1C:
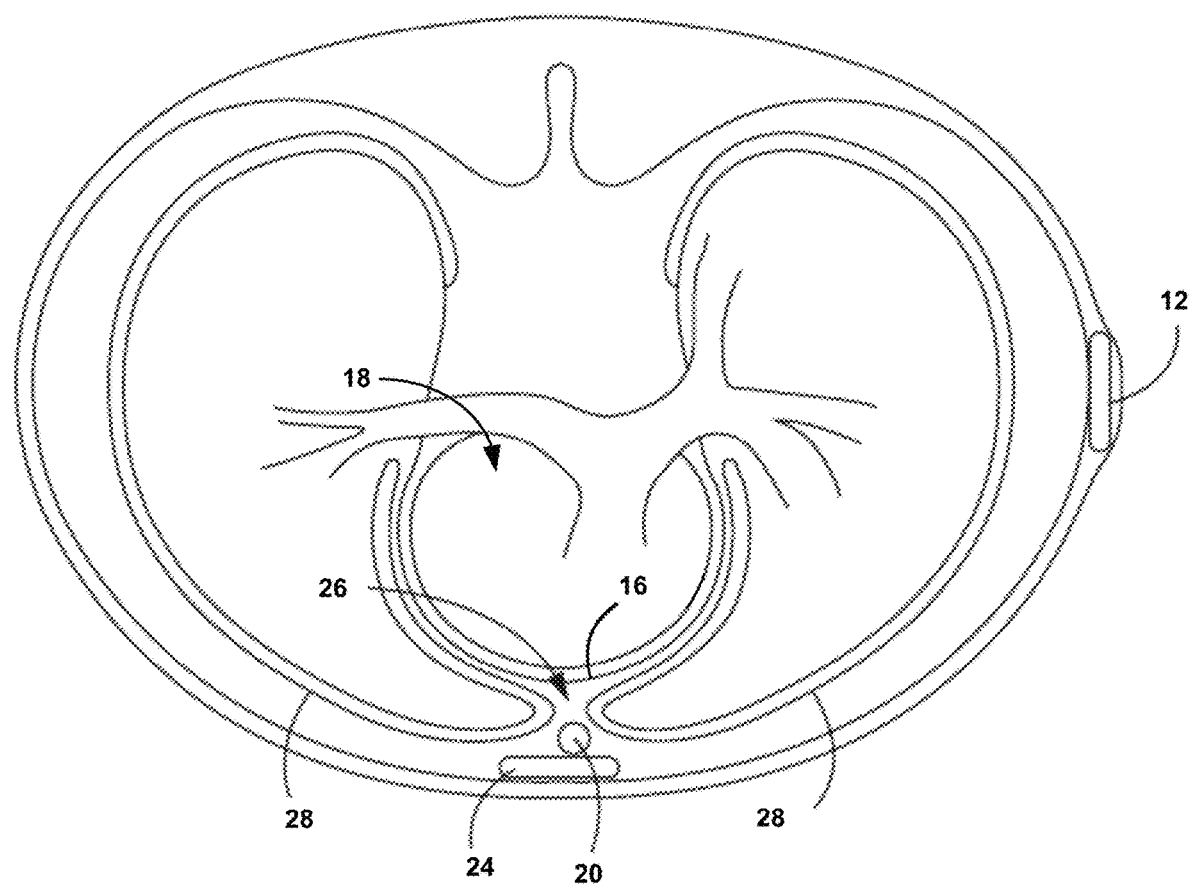

FIGS. 1A-1C are front-view, side-view, and top-view conceptual drawings, respectively, illustrating an example of medical device system 10 (also referred to as "system 10") in conjunction with patient 8. The systems and techniques described herein may be used for lead navigation and positioning during implantation of the lead with an introducer sheath. For example, by providing one or more visible indicators between a proximal and distal portion of a lead of system 10 that indicate a relative longitudinal and radial location of a distal portion of the lead during an implant procedure within an introducer sheath, healthcare providers may implant the lead more safely and efficiently in a way that improves an efficacy of system 10. As discussed above, though FIGS. 1A-1C depict system 10 as implanted near and configured to monitor and/or provide treatment to the cardiac system of patient 8, the implanting procedures and devices described herein may be used for different systems to be implanted at different places for different purposes.

In the illustrated example, the medical device system 10 is an extracardiovascular implantable cardioverter defibrillator (ICD) system implanted within patient 8. However, these techniques may be applicable to other cardiac systems, including cardiac pacemaker systems, cardiac resynchronization therapy defibrillator (CRT-D) systems, cardioverter systems, or combinations thereof, as well as other stimulation and/or sensing systems, such as neurostimulation systems. Further, although described primarily in the context of implanting leads, the techniques may be applicable to implantation of other devices, such as leadless implantable stimulators that including electrodes on their housings. In addition, system 10 may not be limited to treatment of a human patient. In alternative examples, system 10 may be implemented in non-human patients, such as primates, canines, equines, pigs, bovines, ovines, felines, or the like. These other animals may undergo clinical or research therapies that may benefit from the subject matter of this disclosure.

In general, systems (e.g., system 10) may include one or more medical devices, leads, external devices, or other components configured for the techniques described herein. In the illustrated example, system 10 includes an implantable medical device (IMD) 12, which may be an ICD. IMD 12 is connected to at least one implantable cardiac defibrillation lead 20. In some examples, two leads are used. IMD 12 may be configured to deliver high-energy cardioversion or defibrillation pulses to a patient's heart 18 when a ventricular tachyarrhythmias, e.g., ventricular tachycardia (VT) or ventricular fibrillation (VF), is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by IMD 12.

Lead 20 may include indicator 14 that is located between a proximal portion of lead 20 (e.g., a portion of lead 20 that is configured to couple to IMD 12) and a distal portion of lead 20 (e.g., a portion of lead that includes electrodes of lead 20). Indicator 14 may include one or more physical features that make indicator visually distinct from adjacent portions of lead 20, such as a different color, one or more different dimensions (e.g., such as a recess or protrusion), a discrete element secured to lead, or the like. Indicator 14 may be visibly identifiable without the use of image enhancing techniques (e.g., such as fluoroscopy) when indicator 14 is external to patient 8. Further, lead 20 may have a relative amount of stiffness between a distal portion that includes elements that provide therapy or monitoring functionality and indicator 14, such that a relative longitudinal and/or radial orientation of indicator 14 as detected outside of body may reliably indicate a longitudinal and radial orientation of such elements secured to distal portion. Lead 20 may be configured to be implanted in conjunction with an introducer sheath (e.g., such as the introducer sheaths of FIGS. 10A-11B) that is configured to be inserted a predetermined depth into patient 8 at a predetermined location through the skin of patient 8 (e.g., such as one fingerbreadth below the xiphisternal junction). When inserted at the predetermined location to the predetermined depth, the distal portion of introducer sheath may be adjacent a target site to which lead 20 is to be deployed. Once the introducer sheath is thusly inserted, a clinician may insert the distal portion of lead 20 into the introducer and, using indicator 14 (e.g., aligning indicator with an orientation region on the introducer sheath), verify a desired orientation (e.g., an orientation that is expected to be relatively efficacious) of a distal portion of lead 20 at the target site within the introducer sheath. Once the clinician has verified that the distal portion of lead 20 is radially and longitudinally oriented as desired, the clinician may withdraw the introducer sheath to deploy lead 20 and couple a proximal end of lead 20 to IMD 12 and therein implant both.

IMD 12 may be implanted subcutaneously or submuscularly on the left side of patient 8 above the ribcage. Lead 20 may be implanted at least partially in a substernal space, such as at a target site between the ribcage or sternum 24 and heart 18. In one such configuration, a proximal portion of lead 20 may be configured to extend subcutaneously from IMD 12 toward sternum 24 and a distal portion of lead 20 may be configured to extend superior under or below sternum 24 in the anterior medastinum 26 (FIG. 1C). Lead 20 may include one or more curved sections as discussed herein to configure lead 20 to naturally (e.g., in a self-biasing manner) extend in this way upon deployment. In some instances, the target site may substantially in the anterior mediastinum 26. The anterior mediastinum 26 is bounded laterally by the pleurae 28 (FIG. 1C), posteriorly by the pericardium 16 (FIG. 1C), and anteriorly by the sternum 24. In some instances, the anterior wall of the anterior mediastinum may also be formed by the transversus thoracics and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 20 extends along the posterior side of the sternum 24 substantially within the loose connective tissue or substernal musculature of the anterior mediastinum.

In general, "substernal space" may refer to the region defined by the undersurface between sternum 24 and the body cavity but not including pericardium 16. In other words, the region is posterior to the sternum 24 and anterior to the ascending aorta. The substernal space may alternatively be referred to by the terms "retrosternal space" or "mediastinum" or "infrasternal" and may include the region referred to as the anterior mediastinum. Though the term substernal space is used throughout this disclosure for ease of description, it is to be understood that the term is interchangeable with any of the other aforementioned terms. Further, within this disclosure, the term "extra-pericardial" space may refer to a region around the outer heart surface but not within the pericardial sac or space. The region defined as the extra-pericardial space includes the gap, tissue, bone, or other anatomical features around the perimeter of, and adjacent to pericardium 16.

In other examples, lead 20 may be implanted at other extracardiovascular locations, such as being offset laterally to the left or the right of the sternum 24 or located over the sternum 24, or alternatively being configured to extend substantially parallel to the sternum 24 or be angled lateral from the sternum 24 at either the proximal or distal end upon implantation. Although described primarily in the context of delivery of a lead to the substernal space, the systems and techniques described herein may be used to deliver and implant a lead or device in other spaces. For example, techniques as described herein may be used to navigate a medical lead to an implant site in the subcutaneous space. Similarly, lead 20 may be at least partially implanted in other intrathoracic locations, such as other non-vascular, extra-pericardial locations, including the gap, tissue, or other anatomical features around the perimeter of and adjacent to, but not attached to, pericardium 16 or other portion of heart 18 and not above the sternum 24 or ribcage. In an example, the systems and techniques described herein include using indicator 14 to identify a radial and longitudinal orientation of a distal portion of lead 20 where the distal portion is being positioned within the pericardial space.

For example, the distal portion of lead 20 may be guided to a target site within patient 8. To enable such implantation, a distal portion of introducer sheath that is to be inserted to deliver lead 20 may be a length that is configured to extend from a predetermined insertion site (e.g., a site at the introducer sheath is configured to enter patient 8) to a predetermined implantation site across a plurality of patients (e.g., such that most or all patients within a subcategory of gender, height, and/or weight may define substantially similar internal dimensions). As such, once a clinician inserts the introducer sheath at the predetermined incision site the predetermined depth (e.g., such that the distal portion is entirely inserted within patient 8), the clinician may reliably use indicator 14 to track a longitudinal and radial orientation of the distal portion of lead 20 relative to the target site based on how indicator 14 is oriented relative to the introducer sheath.

In an example, lead 20 may be between 45 and 66 centimeters long (e.g., approximately 52 centimeters long) from a distal tip of lead 20 to proximal end that is configured to couple to IMD 12. In some examples, prior to implantation, lead 20 may include a detachable hub that is between 1 and 4 centimeters long that is configured to be used during the implanting lead 20, and/or configured to be used to couple lead 20 to IMD 12, or the like. The introducer sheath may be configured to be inserted through the skin of patient 8 at a predetermined location that is between 1 to 6 centimeters (e.g., approximately 1.5 centimeters or one fingerbreadth) below the xiphisternal junction and may define a distal portion that is between 15 to 22 centimeters long (e.g., approximately 18.6 centimeters long) that is configured to be inserted into patient 8. In some examples, the introducer sheath may also define a proximal portion that includes an entry port that is configured to extend between 1 and 4 centimeters (e.g., approximately 3 centimeters) out of patient. As such, in order to verify that a distal portion of lead 20 is adjacent the target site within introducer sheath, indicator 14 may be between 18 and 25 centimeters (e.g., approximately 21.6 centimeters) from a distal tip of lead 20 such that indicator 14 is viewable when lead 20 is inserted into introducer sheath the predetermined depth.

Lead 20 may include an insulative lead body having a proximal end that includes connector 30 configured to be connected to IMD 12 and a distal portion that includes one or more electrodes. Lead 20 also includes one or more conductors that form an electrically conductive path within the lead body and interconnect the electrical connector and respective ones of the electrodes.

Lead 20 may include defibrillation electrodes 32A, 32B (individually or collectively "defibrillation electrode(s) 32"). In other examples, defibrillation electrodes 32A, 32B may functionally be different sections of a single defibrillation electrode 32, such that both defibrillation electrodes 32 are coupled to the same conductor or are otherwise configured to provide the same electrical stimulation. Though defibrillation electrodes 32 are depicted in FIGS. 1A-1C as coil electrodes for purposes of clarity, it is to be understood that defibrillation electrodes 32 may be of other configurations in other examples, such as an elongated coil electrode. Defibrillation electrodes 32 may be located on the distal portion of lead 20, where the distal portion of lead 20 is the portion of lead 20 that is configured to be implanted as extending along the sternum 24. Lead 20 may be implanted at a target site below or along sternum 24 such that a therapy vector between defibrillation electrodes 32 and a housing electrode formed by or on IMD 12 (or other second electrode of the therapy vector) is substantially across a ventricle of heart 18. The therapy vector may, in one example, be viewed as a line that extends from a point on defibrillation electrodes 32 (e.g., a center of one of the defibrillation electrodes 32) to a point on the housing electrode of IMD 12. As such, it may be advantageous to increase an amount of area across which defibrillation electrodes 32 (and therein the distal portion of lead 20) extends across heart 18. Accordingly, lead 20 may be configured to define a curving distal portion as depicted in FIG. 1A, which may enable lead 20 to provide relatively more efficacious pacing, sensing, and/or defibrillation to heart 18. During deployment, indicator 14 and introducer sheath may be used to verify that lead 20 is radially oriented to properly place electrodes 32, 34 upon deployment to thusly increase an efficacy of system 10.

Lead 20 may also include one or more pace/sense electrodes 34A, 34B (individually or collectively, "pace/sense electrode(s) 34") located on the distal portion of lead 20. Electrodes 34 are referred to herein as pace/sense electrodes because they are generally configured for use in delivery of pacing pulses and/or sensing of cardiac electrical signals. In some instances, electrodes 34 may provide only pacing functionality, only sensing functionality, or both pacing functionality and sensing functionality. In the example illustrated in FIG. 1A and FIG. 1B, pace/sense electrodes 34 are separated from one another by defibrillation electrode 32B. In other examples, however, pace/sense electrodes 34 may be both distal of defibrillation electrode 32B or both proximal of defibrillation electrode 32B. In other examples, lead 20 may include more or fewer electrodes 32, 34 at various locations on lead 20. In some examples, IMD 12 may include one or more electrodes 32, 34 on another lead (not shown). Other lead configurations may be used, such as various electrode arrangements. For example, one or more pace/sense electrodes 34 may be placed between two defibrillation electrodes 32, such as described above. In an example, multiple pace/sense electrodes 34 may be placed between two defibrillation electrodes 32. In an example, two defibrillation electrodes 32 may be adjacent (e.g., such that the two defibrillation electrodes 32 are not separated by any pace/sense electrodes 34 between the two defibrillation electrodes 32). Other arrangements may additionally or alternatively be used.

Lead 20 may define different sizes and shapes as may be appropriate for different purposes (e.g., different patients or different therapies). As discussed above, in some examples, the distal portion of lead 20 may have one or more curved sections. As shown in the example of FIG. 1A, the distal portion of lead 20 is a serpentine shape that includes two "C" shaped curves, which together may resemble the Greek letter epsilon, "ε" Defibrillation electrodes 32 are each carried by one of the two respective C-shaped portions of the lead body distal portion. The two C-shaped curves extend or curve in the same direction away from a central axis of the lead body. Pace/sense electrodes 34 may, in some instances, be approximately aligned with the central axis of the straight, proximal portion of lead 20. In this case, mid-points of defibrillation electrodes 32 are laterally offset from pace/sense electrodes 34. Other examples of extra-cardiovascular leads including one or more defibrillation electrodes and one or more pacing and sensing electrodes 34 carried by curving, serpentine, undulating or zig-zagging distal portion of the lead body 18 that may be implemented with the techniques described herein. In some examples, the distal portion of lead 20 may be straight (e.g., straight or nearly straight).

In an example, the electrode arrangement on lead 20 may correspond to a geometry of lead 20. For example, pace/sense electrodes 34 may be positioned on relative peaks of a curved lead shape, while defibrillation electrodes 32 may be positioned on relative valleys of the curved lead shape. In other examples, the distal portion of lead 20 may include branches, biased portions expanding away from a central shaft, or other shapes (e.g., with one or more electrodes disposed on the branches, shaft, or biased portions) that may provide appropriate monitoring information or therapy. Deploying lead 20 such that electrodes 34, 32 are thusly at these depicted peaks and valleys of serpentine shape may therein increase an efficacy of system 10. For example, electrodes 34, 32 may have access to better sensing or therapy vectors when lead 20 is deployed into the serpentine shape. Orientating the serpentine shaped lead such that pacing/sensing electrodes 34 are closer to heart 18 may provide better electrical sensing of the cardiac signal and/or lower pacing capture thresholds than if pace/sense electrodes 34 were oriented further from heart 18. The serpentine or other shape of the distal portion of lead 20 may have increased fixation to patient 8 as a result of the shape providing resistance against adjacent tissue when an axial force is applied. Another advantage of a shaped distal portion is that electrodes 32, 34 may have access to greater surface area over a relatively shorter length of heart 18. As discussed above, indicator 14 of lead 20 and a respective introducer sheath used to navigate lead 20 to the target site may be used to verify a proper orientation of lead 20 immediately prior to deployment at the substernal target site, therein improving an efficacy of system 10 that employs lead 20.

The systems and techniques described herein may be implemented using different types of leads (e.g., as described above or other lead shapes, lead configurations, and the like), including leads designed for different types of therapies (e.g., cardiac defibrillation, cardiac pacing, spinal cord stimulation, or brain stimulation). The systems and techniques described herein may be implemented using, for example, delivery systems (e.g., a sheath or an elongate tool) or other devices that may be inserted into patient 8 (e.g., the substernal space of the patient).

In general, system 10 may sense electrical signals, such as via one or more sensing vectors that include combinations of pace/sense electrodes 34 and/or a housing electrode of IMD 12. In some examples, IMD 12 may sense cardiac electrical signals using a sensing vector that includes one or both of the defibrillation electrodes 32 and/or one of defibrillation electrodes 32 and one of pace/sense electrodes 34 or a housing electrode of IMD 12. The sensed electrical intrinsic signals may include electrical signals generated by cardiac muscle and indicative of depolarizations and repolarizations of heart 18 at various times during the cardiac cycle. IMD 12 may be configured to analyze the electrical signals sensed by the one or more sensing vectors to detect tachyarrhythmia, such as ventricular tachycardia or ventricular fibrillation. In response to detecting the tachyarrhythmia, IMD 12 may begin to charge a storage element, such as a bank of one or more capacitors, and, when charged, deliver one or more defibrillation pulses via defibrillation electrodes 32 of lead 20 and/or the housing electrode if the tachyarrhythmia is still present. Additionally, or alternatively, IMD 12 may deliver pacing therapy via electrodes 32, 34 and/or the housing electrode of IMD 12. In some examples, the pacing therapy may include antitachycardia pacing (ATP).

System 10 may include external device 22. External device 22 may be a computing device that is configured for use in a home, ambulatory, clinic, or hospital setting to communicate with IMD 12 via wireless telemetry. Examples of communication techniques used by IMD 12 and external device 22 include radiofrequency (RF) telemetry, which may include an RF link established via Bluetooth, wireless local networks, or medical implant communication service (MICS). The communication may include one-way communication in which one device is configured to transmit communication messages and the other device is configured to receive those messages. Alternatively, or additionally, the communication may include two-way communication in which each device is configured to transmit and receive communication messages.

External device 22 may include communication circuitry configured to communicate per the techniques described above. External device 22 may be used to program commands or operating parameters of IMD 12 for controlling functioning of IMD 12 when configured external device 22 is configured as a programmer for IMD 12. External device 22 may be used to communicate with IMD 12 to retrieve data such as operational data, physiological data accumulated in IMD memory, or the like. As such, external device 22 may function as a programmer for IMD 12, an external monitor for IMD 12, or a consumer device such as a smartphone. External device 22 may be coupled to a remote patient monitoring system, such as CARELINK®, available from Medtronic plc, of Dublin, Ireland. A user may use external device 22 to program or update therapy parameters that define therapy or perform other activities with respect to IMD 12. The user may be a physician, technician, surgeon, electrophysiologist, or other healthcare professional. In some examples, the user may be patient 8.

Figure 2A:
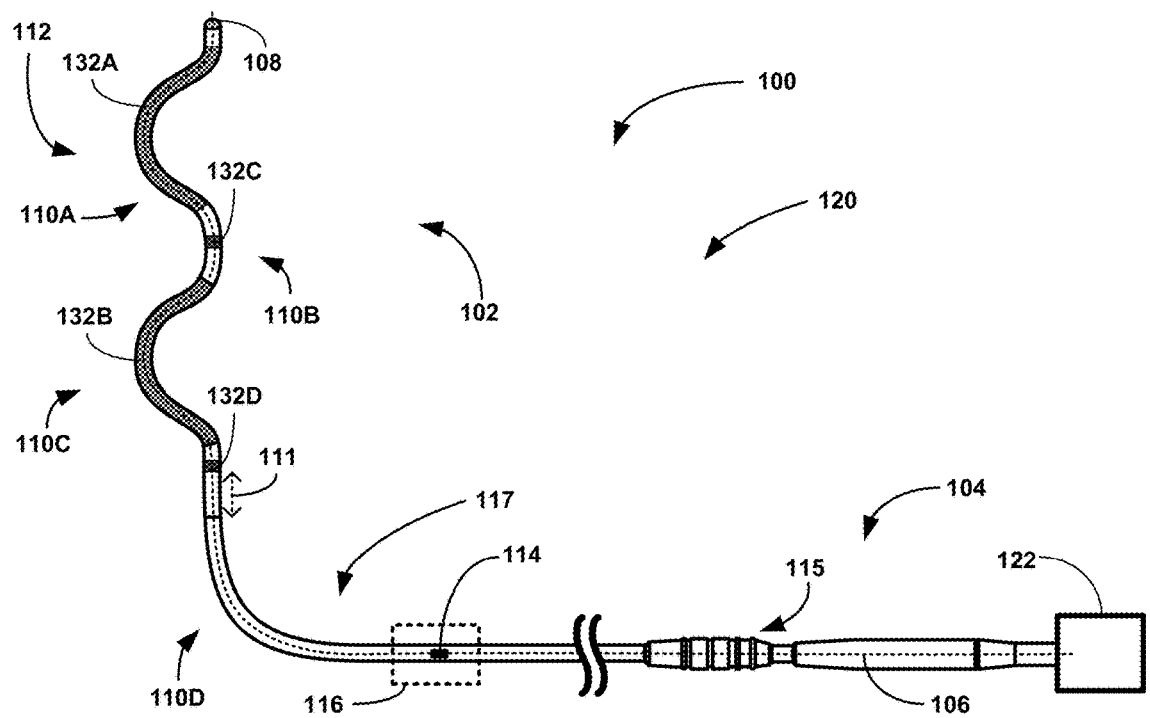
FIGS. 2A and 2B are conceptual and schematic diagrams illustrating a front and back view, respectively, of an example lead in an unconstrained state that includes an example indicator and may be used in the system of FIGS. 1A-1C.
Figure 2C:
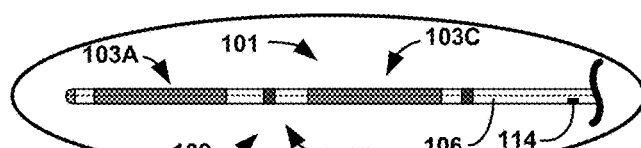
FIG. 2C is a conceptual and schematic diagram illustrating a perspective view of a distal portion and indicator of the lead of FIG. 2A in a constrained state.
Figure 2B:
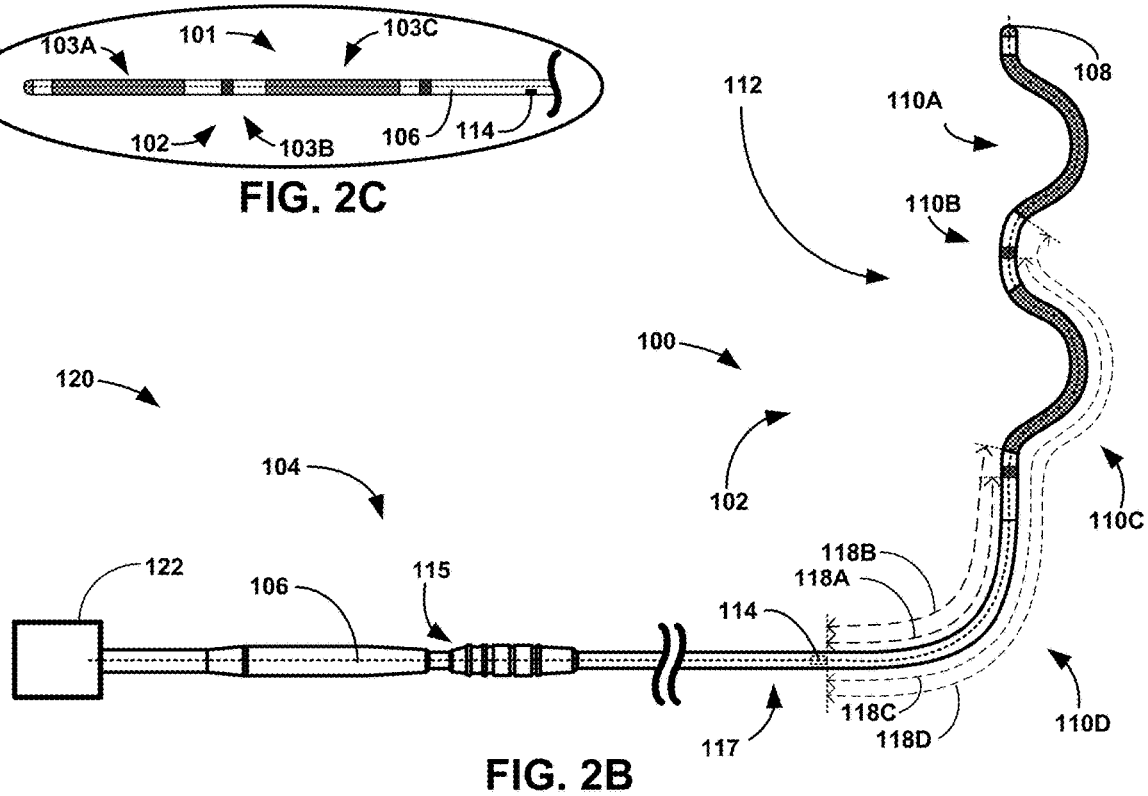

FIGS. 2A and 2B depict conceptual and schematic diagrams of insertable or implantable medical lead 120 as viewed on opposite sides, respectively. Lead 120 may be substantially similar to lead 20 with the exception of any differences described herein. Lead 120 may include distal portion 102 and proximal portion 104. Distal portion 102 of lead 120 may include one or more electrodes 132A-132D (collectively "electrodes").

Electrodes 132 may be similar to defibrillation electrodes 32 and/or pace/sense electrodes 34. For example, electrodes 132A, 132B may be substantially similar to defibrillation electrodes 32, and electrodes 132C, 132D may be substantially similar to pace/sense electrodes 34. In other examples (e.g., for other applications), distal portion 102 of lead 120 may include a different number of electrodes 132, where some function as defibrillation electrodes 32 and others function as pace/sense electrodes 34. The depicted longitudinal length of electrodes 132 of FIGS. 2A and 2B as measured along longitudinal axis 106 of lead 120 is for purposes of illustration only, as in other examples lead 120 may include one or more electrodes 132 that define different longitudinal lengths.

Both FIGS. 2A and 2B depict lead 120 in unconstrained state 100 in which substantially no external forces are applied to lead 120. As depicted, in unconstrained state 100 lead 120 may define serpentine shape 112 as a result of one or more curved sections 110A-110D of distal portion 102 of lead 120. In some examples, curved sections 110 may define serpentine shape 112 along a relatively flat plane, such that lead 120 may define serpentine shape 112 along a predetermined location relative to heart 18 (e.g., across a face of a front of heart 18). In other examples, curved sections 110 may define serpentine shape 112 across a curved plane similar to the curve of lead 20 as depicted in FIG. 1B from the side of patient 8, such that in unconstrained state 100 distal portion 102 of lead 120 arches along an external surface of heart 18.

In some examples, lead 120 may define straight section 111 between curved section 110C and curved section 110D. Straight section 111 may be between 1 and 2 centimeters long (e.g., approximately 1.3 centimeters long). Straight section 111 may be configured to navigate lead 120 away from heart 18 beneath xiphisternal junction for those patients whose heart 18 sits at a location that is relatively more cranial within the chests of the respective patients. Put differently, by including straight section 111, lead 120 may be configured to be properly radially and longitudinally oriented when indicator 114 is aligned with an orientation region of an indicator sheath for a greater range of patients, as described herein.

Deploying lead 120 such that lead 120 defines serpentine shape 112 as deployed may improve an efficacy of lead 120 (and/or medical system 10). For example, as discussed herein, serpentine shape 112 may improve an array or a trajectory of therapy vectors available to electrodes 132 of lead 120. Further, serpentine shape 112 may promote a level or quality of fixation of lead 120 to patient 8 at the desired implant location as a result of serpentine shape 112 providing resistance against tissue of patient 8 when an axial force is applied. Further, serpentine shape 112 may enable a relatively higher amount of electrode 132 surface area to face heart 18 while occupying a relatively small amount of vertical space across the face of heart 18 (such that electrodes 132 substantially avoid extending past a "top" or "bottom" of heart as implanted). Increasing an amount of surface area of electrodes 132 facing heart 18 may increase an efficacy of system 10 that utilizes lead 120 and heart 18, particularly where electrodes 132 are similar to defibrillation electrodes 32.

An efficacy of system 10 that utilizes lead 120 may be impacted by whether serpentine shape 112 is properly oriented when implanted by heart 18. For example, lead 120 and therein system 10 may have an improved efficacy when serpentine shape 112 is defined as depicted in FIG. 2A across the face of heart 18. Deploying lead 120 such that lead 120 defines serpentine shape 112 where electrodes 132A, 132B extend toward a right side of patient 8 may enable electrodes 132 to create a tunneling zone to left side of patient 8 while pushing a defibrillation vector to a right side of patient 8. Similarly, deploying lead 120 such that lead 120 defines serpentine shape 112 where electrodes 132C, 132D extend toward a left side of patient 8 may locate electrodes 132 closer to ventricles of heart 18 to improve an ability to sense and/or pace heart 18. Conversely, accidentally deploying lead 120 such that lead 120 defines serpentine shape 112 in a different direction (e.g., with electrodes 132A, 132B curving toward a right side of patient 8) might compromise an efficacy of system 10, such that it is important to properly radially align lead 120 during deployment/implantation. For example, deploying lead 120 such that lead 120 defines serpentine shape 112 in a different direction may result in lead 120 sending a defibrillation vector toward a left side of patient 8 such that a relatively smaller amount of heart 18 is within therapy vectors provided by lead 120, and/or deploying lead 120 such that serpentine shape 112 is defined in a different relative direction within patient 8 may increase a distance between the ventricles of heart 18 and pacing and/or sensing electrodes 132 of lead 120 such that it is relatively more difficult to sense and/or pace heart 18.

Curved sections 110 may be configured to resiliently cause distal portion 102 of lead 120 to define serpentine shape 112, such that if a force causes distal portion 102 to another shape curved sections 110 may reliably and repeatedly cause distal portion 102 to again define serpentine shape 112 once the force is reduced or eliminated. For example, curved sections 110 may have a shape memory that corresponds to serpentine shape 112, or curved sections 110 may include one or more deformation members (e.g., such as wires that are in tension) within lead 120 that cause distal portion 102 to define serpentine shape 112, or curved sections 110 may include notches or compound walls that cause distal portion 102 to define serpentine shape 112, or the like.

In some examples, some curved sections 110A, 110B, 110C are configured to cause lead 120 to define serpentine shape 112, and other curved sections 110D are configured to cause lead 120 to extend from a target site to IMD 12 as implanted. For example, curved sections 110A-110C may cause distal portion 102 of lead 120 to define serpentine shape 112 under sternum 24 of patient 8, while curved section 110D may be configured to cause proximal portion 104 of lead 120 to extend toward a left should of patient 8 toward an implant site of IMD 12. Where IMD 12 was implanted at a different site, lead 120 may include more or different curved sections 110D that are configured to cause lead 120 to curve from a site at which electrodes 132 provide monitoring or therapy provision functionality to a site at which IMD 12 is implanted.

Lead 120 may include visible indicator 114 at a predetermined longitudinal location along lead 120. Indicator 114 may be an element or feature of lead 120 that is visible to a naked eye without the use of image-enhancement techniques such as x-ray, fluoroscopy, magnifying glasses, or the like. Indicator 114 may be visible as a result of indicator 114 being visually distinct from longitudinally adjacent and circumferentially adjacent portions of lead 120 as depicted and discussed herein. For example, indicator 114 may be a different color than longitudinally and circumferentially adjacent portions of lead 120, and/or indicator 114 may include a physically distinct element (e.g., a recess or protrusion) that is different than longitudinally and/or circumferentially adjacent portions of lead 120. In some examples, indicator 114 may be part of a unitary structure with longitudinally and circumferentially adjacent portions of lead 120, though in other examples indicator 114 may include one or more discrete components fixedly secured to lead 120.

Indicator 114 may also be located at a predetermined radial location along a radius of lead 120. For example, indicator 114 may be located on a side of lead 120 that is configured to be "face up" (e.g., visible to a clinician) as the clinician inserts lead 120 into patient 8, e.g., in the orientation described with regard to FIGS. 1A-1C. For example, where lead 120 is configured to be inserted to a substernal site, indicator 114 may be on a face of lead 120 where proximal portion 104 extends to the right of indicator (e.g., as viewed from the face of lead 120) and first curved section 110C curves away from proximal portion 104 after which second curved section 110B curves back toward proximal portion 104. Put differently, indicator 114 may be located on lead 120 such that, during an insertion procedure, indicator 114 is facing away from patient 8 and is instead facing clinician, where an introducer sheath and lead 120 are between patient 8 and the clinician. In this manner, the clinician may verify and/or correct what the radial orientation of lead 120 will be upon deployment of lead 120 from constrained state 101 within an introducer sheath to unconstrained state 100 when lead 120 is already navigated to the target site and is ready to deploy immediately upon such verification and/or correction. For example, as discussed herein, a "correct" radial orientation in unconstrained state 100 may include the first curve 110C will arch toward a right side of patient 8, second curve 110B will arch in an opposite direction toward a left side of patient 8, and third curve 110A will arch back toward a right side of patient 8. Further, lead 120 may define another curve that arches toward an implantation site of IMD 12. For examples, where IMD 12 is implanted at a subclavical location, curve 110D will arch proximal portion 104 toward a left shoulder of patient 8. Further, by enabling the clinician to verify and/or correct what the radial orientation will be upon deployment from constrained state 101 within an introducer sheath to unconstrained state 100 without forcing the clinician to focus away from lead 120 (e.g., by avoiding the use of other tools or devices such as a fluoroscopy monitor that would require the clinician to look elsewhere), indicator 114 and the introducer sheath may improve a reliably and simplicity (and therein potentially safety) of the implant procedure related to lead 120.

Lead 120 may be configured to be straightened when received by an introducer sheath. FIG. 2C is a conceptual and schematic diagram depicting constrained state 101 in which lead 120 is straightened as lead 120 is inserted within an introducer sheath. As depicted, curved sections 110 may be relatively straight when in constrained state 101. An amount of deformation that takes place when transitioning between constrained 101 and unconstrained states 100 may be predetermined, such that an eventual shape that will be defined by lead 120 in unconstrained state 100 may be accurately predicted based on the relative longitudinal and radial orientation of lead 120 in constrained state 101 immediately prior to deployment.

Lead 120 may be configured such that longitudinal movement of indicator 114 correlates with longitudinal movement of distal portion 102 of lead 120, and radial movement of indicator 114 correlates with radial movement of distal portion 102 of lead 120. For example, lead 120 may be relatively longitudinally stiff, such that there is a substantially 1:1 relationship between proximal or distal movement of indicator 114 and corresponding proximal or distal movement of distal portion 102, respectively. In this way, indicator 114 and electrodes 132 may define predetermined longitudinal distances 118A-118D (collectively "predetermined longitudinal distances 118) between each other. In some examples, lead 120 may be between 45 and 70 centimeters long, a longitudinal distance between indicator 114 and distal tip 108 of lead 120 may be between 18 and 24 centimeters, and each of predetermined longitudinal distances 118 may be less than the longitudinal distance between indicator 114 and distal tip 108 such that electrodes 132 are predetermined to fall at efficacious locations on serpentine shape 112. In some examples, predetermined longitudinal distance 118A may be between 10 and 12 centimeters, predetermined longitudinal distance 118B may be between 11 centimeters and 13 centimeters, predetermined longitudinal distance 118C may be between 15 centimeters and 17 centimeters, and predetermined distance 118D may be between 16 centimeters and 18 centimeters. For example, lead 120 may include indicator 114 a longitudinal distance of approximately 21.6 centimeters from distal tip 108, defines longitudinal distance 118A to proximal end of pace/sense electrode 132D as approximately 10.96 centimeters, defines longitudinal distance 118B to proximal end of defibrillation electrode 132B as approximately 11.74 centimeters, defines longitudinal distance 118C to proximal end of pace/sense electrode 132C as approximately 16.30 centimeters, and defines longitudinal distance 118D to proximal end of defibrillation electrode 132A as approximately 17.10 centimeters. Where lead 120 defines these approximate dimensions, lead 120 may be properly longitudinally and radially oriented when inserted into an introducer sheath that is inserted to a predetermined depth through the skin of patient 8 approximately 1.5 centimeters below xiphisternal junction for approximately 95% of adult patients when indicator 114 is aligned with the orientation region of the introducer sheath as described herein.

Similarly, lead 120 may be configured such that there is an approximately 1:1 relationship between radial (e.g., twisting) movement of indicator 114 and corresponding radial movement of distal portion 102 of lead 120. For example, as depicted in FIG. 2A, indicator 114 is visible to a clinician viewing from the perspective shown in FIG. 2A, but as lead 120 is flipped such that the position of distal portion 102 relative to proximal portion 104 of lead 120 is reversed, indicator 114 is hidden (as indicated by the dotted lines). Further, in some examples, lead 120 may include hub 122 at proximal end of lead 120. Hub 122 may include one or more ports (not depicted) for manipulating lead 120. In some examples, hub 122 may be used to push lead 120 into an introducer sheath. Hub 122 may include an element configured to seal lead 120 to IMD 12 upon implantation. In some examples, some or all of hub 122 is configured to be remove following insertion and prior to securing lead 120 to IMD 12. While hub 122 is depicted as a box in FIGS. 2A and 2B, it is to be understood that hub 122 may take substantially any shape consistent with aspects of this disclosure.

In some examples, lead 120 may include anchoring sleeve 115. Anchoring sleeve 115 may extend around a full circumference of an outer surface of lead 120. Anchoring sleeve 115 may be configured to be secured to patient 8 adjacent the xiphoid incision upon implantation. A clinician may secure lead 120 within patient by suturing anchoring sleeve 115 to patient 8 at the xiphoid incision. Anchoring sleeve 115 may be configured to be slideable over at least some of lead 120 (e.g., move longitudinally in relation to lead 120) before anchoring sleeve 115 is secured to patients 8 using sutures. Anchoring sleeve 115 may be configured to be slideable over a length of lead 120 that defines an anchoring interface to which anchoring sleeve 115 may be interlocked when anchoring sleeve 115 is secured to patient 8. For example, anchoring sleeve may move longitudinally over anchoring portion 117 of tubing that has been had predetermined shapes laser-ablated into a tubing overlay. The ablated predetermined shapes may be substantially similar to shapes that extend inward from an inner surface of anchoring sleeve 115, such that an anchoring sleeve 115 may interlock with these ablated shapes of anchoring portion 117 when anchoring sleeve 117 is compressed from the sutures. In this way, a clinician may position an anchoring sleeve 117 over a portion of anchoring portion 117 that is adjacent xiphoid incision once lead 120 is inserted into patient 8.

Lead 120 may define anchoring portion 117 such that anchoring portion 117 extends proximally from a distal end that is between 1 and two centimeters from a proximal edge of electrode 132D. In some examples, anchoring portion 117 extends proximally from a location that is immediately proximal to straight section 111. Anchoring portion 117 may longitudinally extend proximal from straight section 111 for between 9 and 12 centimeters. For example, anchoring portion 117 may be 10.7 centimeters long as measured along longitudinal axis 106 of lead 120. These lengths may enable lead 120 to define anchoring portion 117 adjacent xiphoid incision upon insertion of lead 120 for a vast majority (e.g., 95%) of adult patients.

Figure 3:
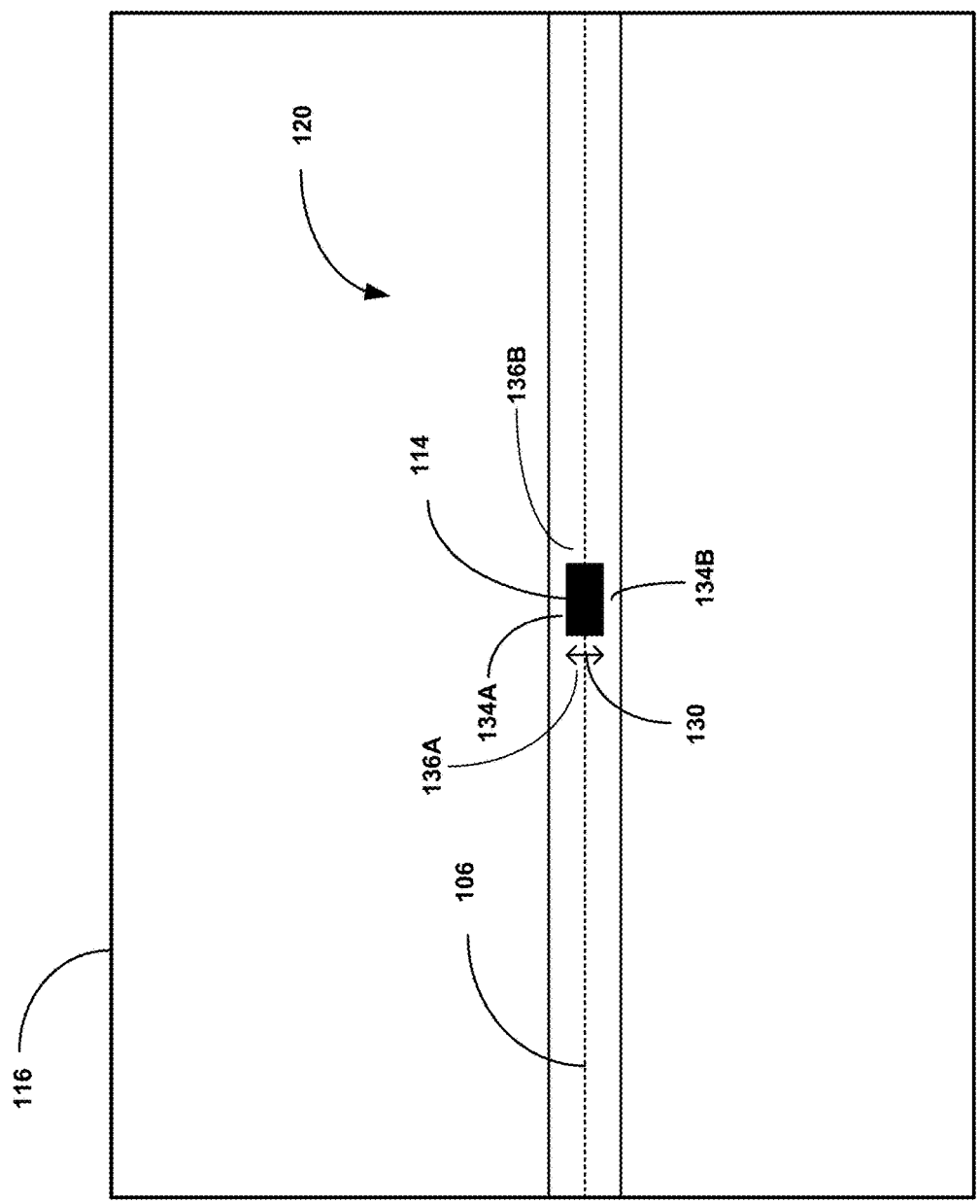
FIG. 3 is a conceptual and schematic diagram illustrating the visible indicator of FIG. 2A.

A conceptual and schematic diagram illustrating detail view 116 of FIG. 2A is depicted in FIG. 3. Detail view 11 includes indicator 114 of lead 120. Though indicator 114 is depicted as defining a rectangular shape, it is to be understood that indicator 114 may define any shape that is consistent with this disclosure. Indicator 114 may be configured to indicate a relative rotational/radial orientation of lead 120 (e.g., relative to other components that are not fixedly secured to lead 120). Indicator 114 may be configured to indicate a relative rotational/radial orientation of lead 120 by virtue of indicator 114 extending portion 130 around perimeter of lead 114 along a plane that it is substantially perpendicular to longitudinal axis 106 of lead 120 rather than extending around the full perimeter. As such, there may be circumferentially adjacent portions 134A, 134B (collectively, "circumferentially adjacent portions 134") of lead 120 on either side of indicator 114 on a plane that is perpendicular to longitudinal axis 106 of lead 120. In some examples (not depicted), indicator 114 may narrow to a relatively narrower end on one or both longitudinal ends of indicator 114, to improve an ability of a clinician visually identifying a radial orientation of lead 120 using indicator 114. Further, as depicted, indicator 114 may be a different color than circumferentially adjacent portions 134 of lead 120 and/or longitudinally adjacent portions 136A, 136B (collectively, "longitudinally adjacent portions 136") of lead 120.

Figure 4:
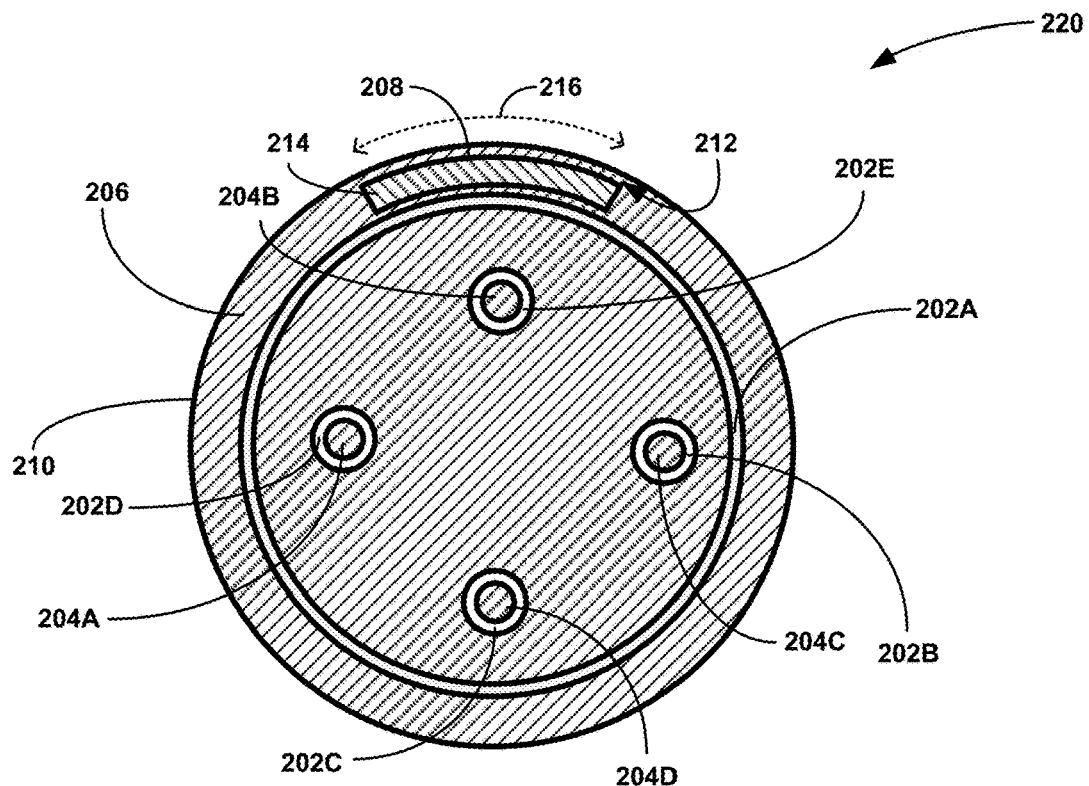
FIG. 4 is a conceptual and schematic diagram illustrating a cross-sectional view of an example lead that includes an example indicator that is embedded in an outer layer of the lead.

FIG. 4 is a conceptual and schematic diagram illustrating a cross-sectional view of an example lead 220 including an example indicator 214. Lead 220 may be substantially similar to lead 20 and lead 120 with the exception of any differences described herein, and indicator 214 may be substantially similar to indicator 114 with the exception of any differences described herein. Lead 220 may define one or more longitudinal lumens 202A-202E (collectively, "lumens 202"). Lumens 202 may house one or more components such as electrical conductors 204A-204D (collectively, "electrical conductors 204"). Lead 220 may be configured to couple electrical conductors 204 to one or more electrodes (e.g., such as electrodes 32, 34, 132) at a distal end of lead 220 and couple electrical conductors 204 to an IMD (e.g., such as IMD 12) at a proximal end of lead 220.

As depicted in FIG. 4, indicator 214 may be a discrete component that is embedded in outer layer 206 of lead 220. Indicator 214 may be configured to define a radial distance between outer surface 208 of indicator 214 and outer surface 210 of lead 220, such that portion 212 of lead 220 longitudinally extends along a longitudinal length of indicator 214 to separate indicator 214 from outer surface 210 of lead 220. Some or all of indicator 214 may be visible through portion 212. For example, portion 212 may be relatively translucent to enable some or all of indicator 214 to be visible through portion 212. In some instances, indicator 214 may be colored differently than circumferentially and/or longitudinally adjacent portions of lead 220. Indicator 214 may extend around a perimeter of lead 220 radial distance 216 that is less than a full circumference of lead 220.

Figure 5:
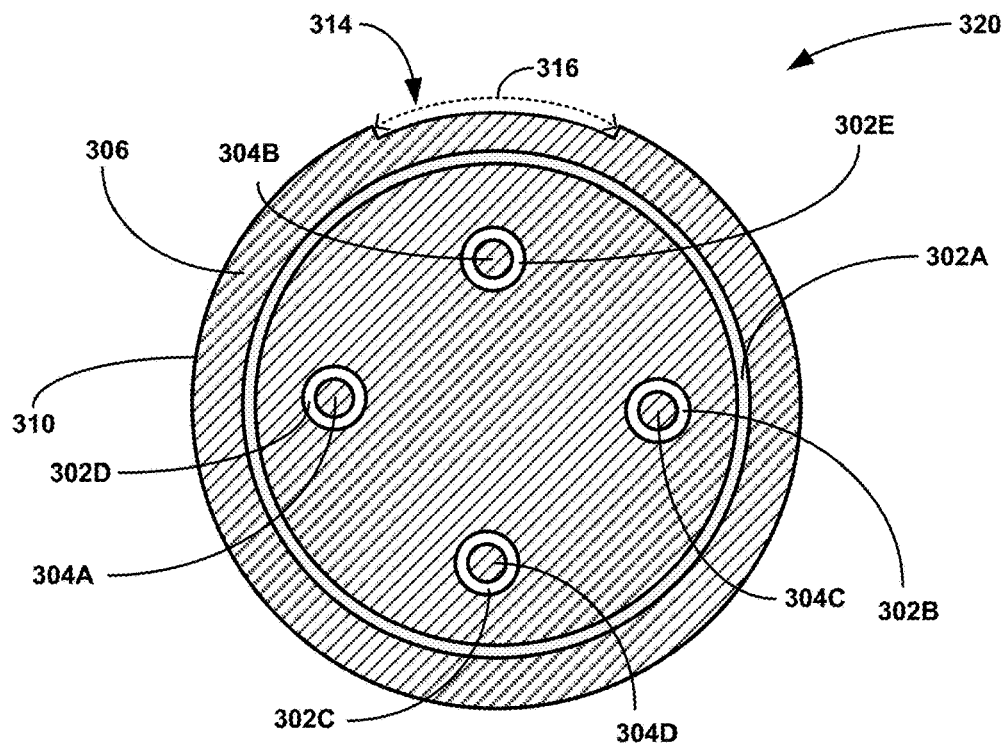
FIG. 5 is a conceptual and schematic diagram illustrating a cross-sectional view of an example lead that includes an example indicator that is recessed from an outer surface of the lead.

FIG. 5 is a conceptual and schematic diagram illustrating a cross-sectional view of an example lead 320 including an example indicator 314. Lead 320 may be substantially similar to lead 20, lead 120, and lead 220 with the exception of any differences described herein, and indicator 314 may be substantially similar to indicator 114 and indicator 214 with the exception of any differences described herein. Lead 320 may define one or more longitudinal lumens 302A-302E (collectively, "lumens 302"). Lumens 302 may house one or more longitudinal components such as electrical conductors 304A-304D (collectively, "electrical conductors 304"). Lead 320 may be configured to couple electrical conductors 304 to one or more electrodes (e.g., such as electrodes 32, 34, 132) at a distal end of lead 320 and couple electrical conductors 304 to an IMD (e.g., such as IMD 12) at a proximal end of lead 320.

As depicted in FIG. 5, indicator 314 may include a recess that is recessed radially inward from outer surface 310 of outer layer 306 of lead 320. Indicator 314 may extend into outer surface 310 of lead 320 a distance sufficient to make indicator 314 visibly detectable by a clinician. In some instances, some or all of indicator 314 may be colored differently than circumferentially and/or longitudinally adjacent portions of lead 320. Indicator 314 may extend around a perimeter of lead 320 radial distance 316 that is less than a full circumference of lead 320.

Figure 6:
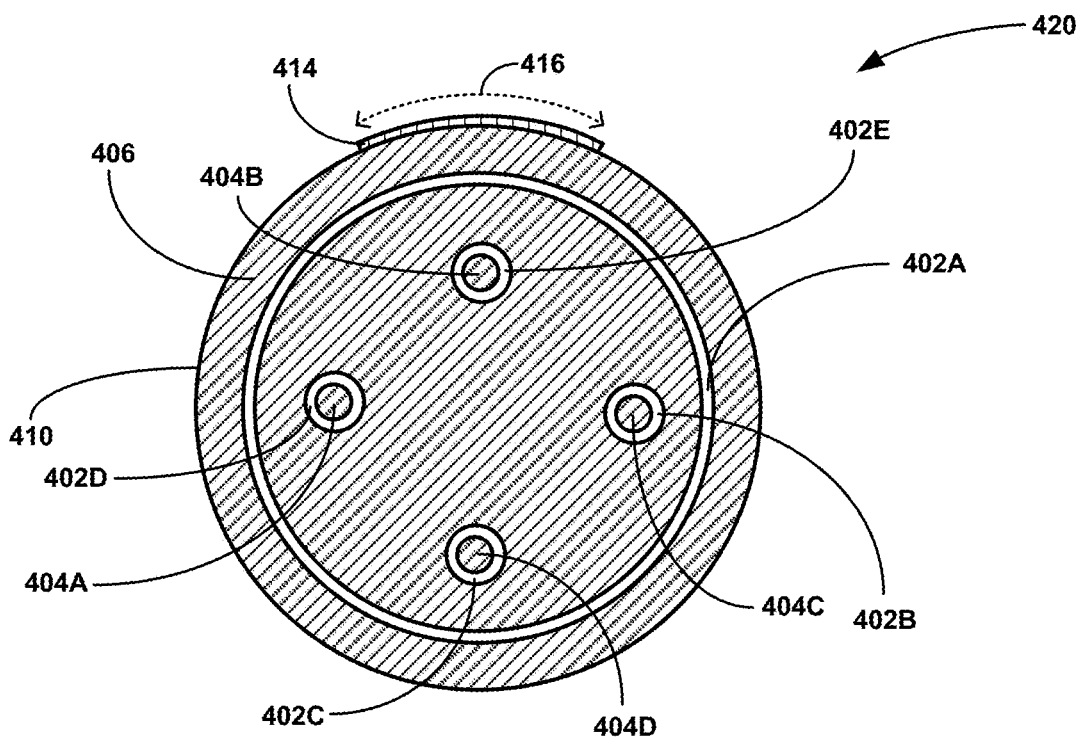
FIG. 6 is a conceptual and schematic diagram illustrating a cross-sectional view of an example lead that includes an example indicator that includes a discrete component secured to an outer surface of the lead.

FIG. 6 is a conceptual and schematic diagram illustrating a cross-sectional view of an example lead 420 including an example indicator 414. Lead 420 may be substantially similar to lead 20, lead 120, lead 220, and lead 320 with the exception of any differences described herein, and indicator 414 may be substantially similar to indicator 114, indicator 214, and indicator 314 with the exception of any differences described herein. Lead 420 may define one or more longitudinal lumens 402A-402E (collectively, "lumens 402"). Lumens 402 may house one or more longitudinal components such as electrical conductors 404A-404D (collectively, "electrical conductors 404"). Lead 420 may be configured to couple electrical conductors 404 to one or more electrodes (e.g., such as electrodes 32, 34, 132) at a distal end of lead 420 and couple electrical conductors 404 to an IMD (e.g., such as IMD 12) at a proximal end of lead 420.

As depicted in FIG. 6, indicator 414 may include a discrete component that is secured to outer surface 410 of outer layer 406 of lead 420. Indicator 414 may extend radially out from outer surface 410 of lead 420 a distance sufficient to make indicator 414 visibly detectable to a clinician. In some instances, some or all of indicator 414 may further be colored differently than circumferentially and/or longitudinally adjacent portions of lead 420. Indicator 414 may extend around a perimeter of lead 420 a radial distance 416 that is less than a full circumference of lead 420.

Figure 7:
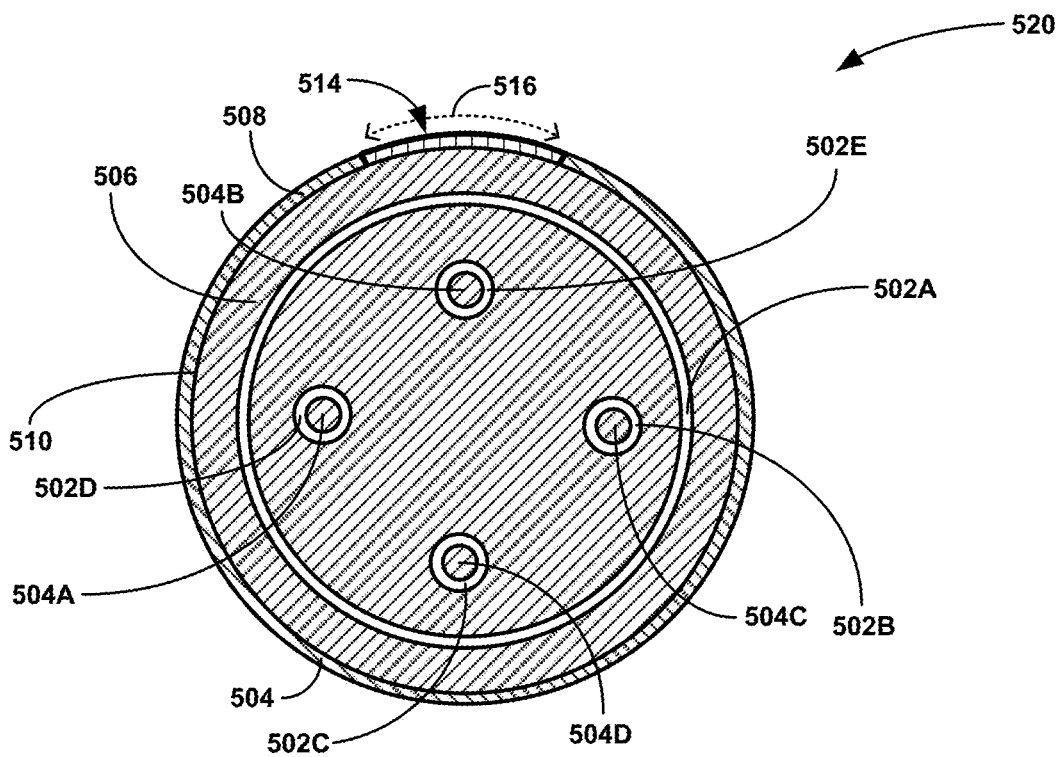
FIG. 7 is a conceptual and schematic diagram illustrating a cross-sectional view of an example lead that includes an example indicator that is portion of a sheath that is secured to an outer surface of the lead.

FIG. 7 is a conceptual and schematic diagram illustrating a cross-sectional view of an example lead 520 including an example indicator 514. Lead 520 may be substantially similar to lead 20, lead 120, lead 220, lead 320, and lead 420 with the exception of any differences described herein, and indicator 514 may be substantially similar to indicator 114, indicator 214, indicator 314, and indicator 414 with the exception of any differences described herein. Lead 520 may define one or more longitudinal lumens 502A-502E (collectively, "lumens 502"). Lumens 502 may house one or more longitudinal components such as electrical conductors 504A-504D (collectively "electrical conductors 504"). Lead 520 may be configured to couple electrical conductors 504 to one or more electrodes (e.g., such as electrodes 32, 34, 132) at a distal end of lead 520 and couple electrical conductors 504 to an IMD (e.g., such as IMD 12) at a proximal end of lead 520.

As depicted in FIG. 7, indicator 514 may include a portion of sleeve 508 that is secured to outer surface 510 of outer layer 506 of lead 520. For example, sleeve 508 may be a film that is placed over lead 520 at the appropriate longitudinal position and then heat shrunk onto lead 520 at that position. In some instances, sleeve 508 and/or indicator 514 may be colored differently than longitudinally adjacent portions of lead 520. For example, sleeve 508 may be a first color that is different than a second color of longitudinally adjacent portions of lead 520, and indicator 514 may be a third color that is different than either first color or second color. Within sleeve 508, indicator 514 may extend around a perimeter of lead 520 radial distance 516 that is less than a full circumference of lead 520. Sleeve 508 may be secured to a full circumference of outer surface 510 of lead 520. Sleeve 508 may define a longitudinal length that is substantially similar to indicator 514, where longitudinal length of both sleeve 508 and indicator 514 is a relatively small amount of longitudinal length of lead 520. As a result of sleeve 508 extending around a full circumference of lead 520 and having a substantially similar longitudinal length as indicator 514, sleeve 508 may function as a longitudinal indicator for lead 520, indicating when lead 520 is inserted to a proper depth. When inserted to a proper depth as indicated by sleeve 508, a clinician may rotate lead 520 until indicator 514 is properly radially aligned. In this way, sleeve 508 may be configured to indicate proper longitudinal orientation during insertion, while indicator 514 may be configured to indicate proper radial orientation as well as potentially proper longitudinal orientation as discussed herein.

Figure 8A:
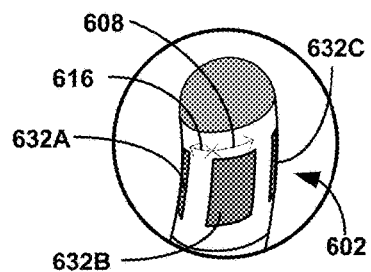
FIGS. 8A-8C are conceptual and schematic diagrams illustrating a perspective view of a distal end, a front unconstrained view, and a front constrained view, respectively, of an example lead with an example indicator.
Figure 8B:
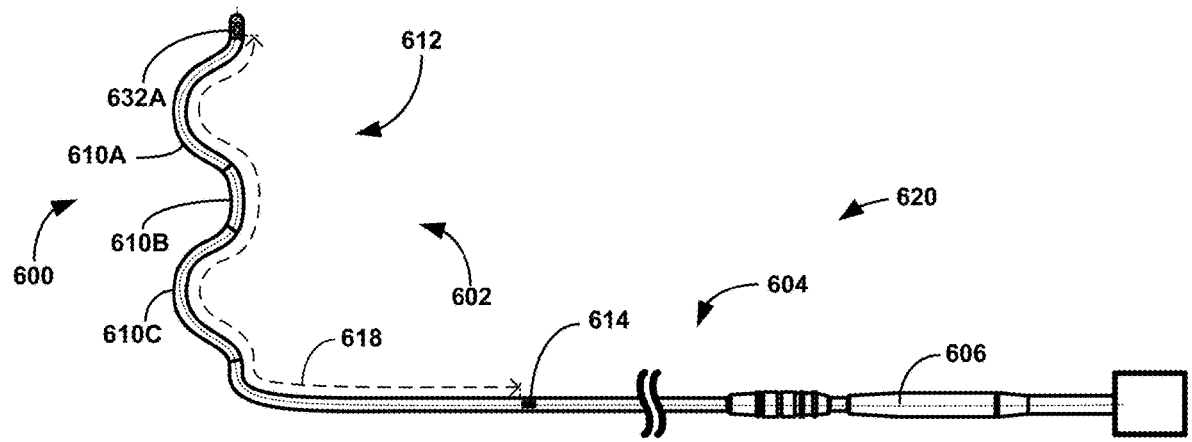
Figure 8C:
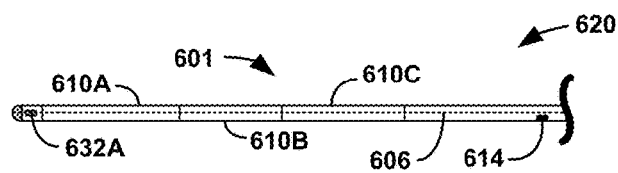

In some examples, aspects of this disclosure may relate to leads that includes segmented electrodes or the like at a distal end, such as for applications where a lead is to be implanted in a brain for deep brain stimulation (DBS) or application where a lead is to be implanted adjacent a spinal cord for spinal cord stimulation (SCS). For example, FIGS. 8A-8C depict conceptual and schematic diagrams of insertable or implantable medical lead 620 with one or more segmented electrodes 632 as viewed from a distal end, from a front view in an unconstrained state, and from a front in a constrained state, respectively. Lead 620 may be substantially similar to lead 20, lead 120, lead 220, lead 320, lead 420, and lead 520 with the exception of any differences described herein. Similarly, lead 620 may include indicator that is substantially similar to indicator 14, indicator 114, indicator 214, indicator 314, indicator 414, and indicator 514 with the exception of any differences discussed herein.

Lead 620 may include distal portion 602 and proximal portion 604. Distal portion 602 of lead 620 may include one or more electrodes 632. Electrodes 632 may be similar to defibrillation electrodes 32 and/or pace/sense electrodes 34. One or more electrodes 632 of lead 620 may be segmented electrodes with a radial component, such that one or more electrodes 632 extend out of less than 360° of a radial perimeter of lead 620. Put differently, one or more electrodes 632 may only radially extend out from lead 620 along a portion of a plane that is perpendicular to longitudinal axis 606 of lead 620. For example, FIG. 8A depicts a conceptual and schematic diagram illustrating isometric view of some of distal portion 602 of lead 620. As depicted, distal portion 602 includes electrodes 632B, 632A, 632C. Each of electrodes 632A, 632B, 632C extend around portion 608 of perimeter of lead 620. As such, each of electrodes 632A, 632B, 632C may define circumferential gap 616 between itself and radially adjacent electrodes 632A, 632B, 632C. In other examples, lead 620 may include a different number of electrodes along one plane that is perpendicular to longitudinal axis 606 of lead 620, such as only one electrode 632 that extends 170° around lead 620 or four electrodes 632 that each extend 80° around lead 620. In such examples, each electrode 632 of lead 620 may extend around a portion 608 of perimeter of lead 620 that is less than 360° around lead 620.

The circumferential length of portion 608 is depicted for purposes of illustration only, as one or more of electrodes 632 may define a greater or smaller circumferential length than portion 608. For example, electrode 632 may extend 45° around longitudinal axis 606 of lead 620, 90° around longitudinal axis 606 of lead 620, 180° around longitudinal axis 606 of lead 620, or the like.

FIG. 8B depict lead 620 in unconstrained state 600 in which substantially no external forces are applied to lead 620. As depicted, in unconstrained state 600 lead 620 may define serpentine shape 612 as a result of one or more curves 610A-610C of distal portion 602 of lead 620. Curves 610 may define serpentine shape 612 along a relatively flat plane.

However, lead 620 may be straightened when inserted through an introducer sheath. FIG. 8C is a conceptual and schematic diagram depicting constrained state 601 in which lead 620 is straightened as lead 620 is inserted within an introducer sheath. As depicted, curved sections 610 may be relatively straight when in constrained state 601. Further, as a result of curved sections 610 straightening, indicator 614 may be offline relative to electrode 632 (e.g., such that indicator 614 and electrode 632 are no longer aligned with longitudinal axis 606 as depicted in FIG. 8C). In other examples (not depicted), indicator 614 and electrode 632 may remain aligned similarly in both constrained state 600 and unconstrained state 601. Whether or not indicator 614 and electrode 632 are aligned in both constrained state 600 and unconstrained state 601 and an amount (if any) that indicator 614 and electrode 632 are not constrained may be predetermined, such that electrode 632 may be properly rotationally aligned as discussed herein when in constrained state 601.

Lead 620 may be configured such that longitudinal movement of indicator 614 correlates with longitudinal movement of one or more electrodes 632, and radial movement of indicator 614 correlates with radial movement of one or more electrodes 632. For example, lead 620 may be relatively longitudinally stiff, such that there is a substantially 1:1 relationship between proximal or distal movement of indicator 614 and corresponding proximal or distal movement of electrodes 632, respectively. In this way, indicator 614 and electrodes 632 may define predetermined longitudinal distance 618 between each other. For example, where lead 620 is 52 centimeters long, the predetermined longitudinal distance 618 may be just under 21.6 centimeters.

Similarly, lead 620 may be configured such that there is a substantially 1:1 relationship between radial (e.g., twisting) movement of indicator 614 and corresponding radial movement of one or more electrodes 632. It should be noted that, while indicator 614 and electrodes 632 are depicted as on the same side of lead 620 for purposes of clarity (e.g., such that both indicator 614 and electrode 632 are visible and oriented outward in FIG. 8B), in other examples indicator 614 and electrode 632 may be on opposite sides of lead 620, or indicator 614 and electrode 632 may be otherwise radially offset from each other.

Figure 9:
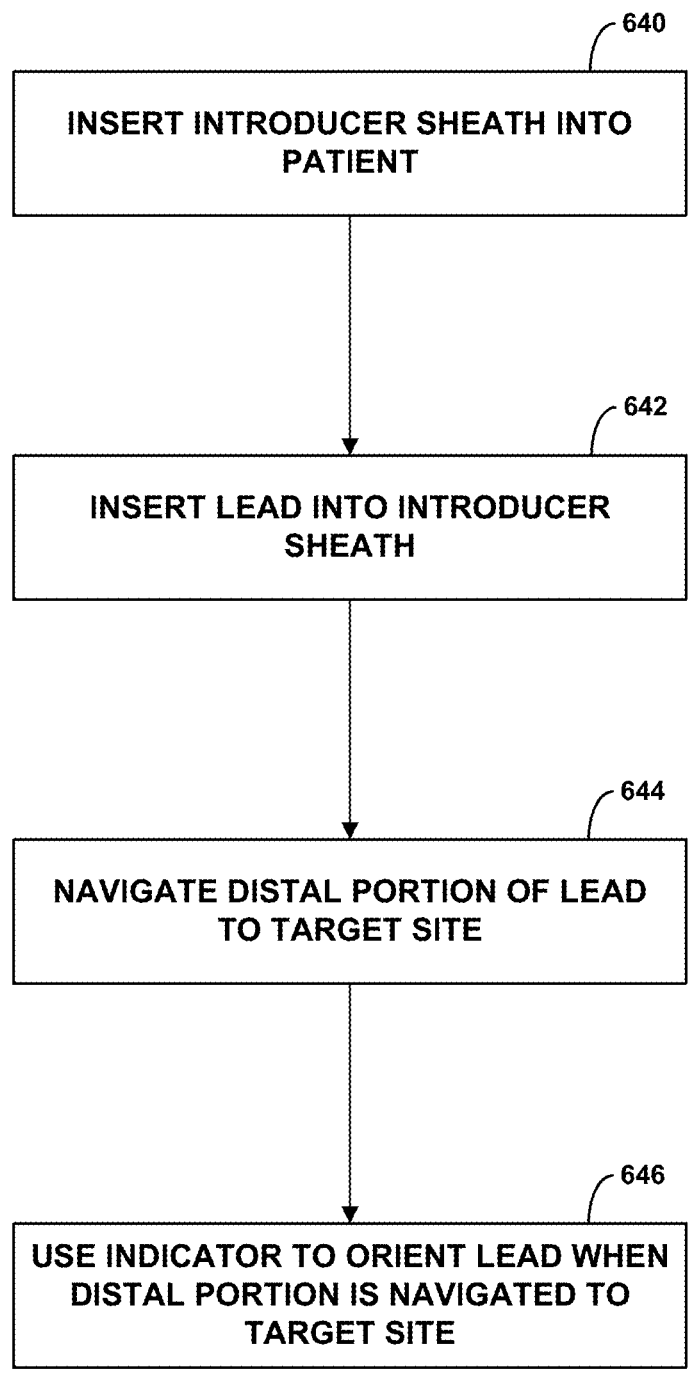
FIG. 9 is a flowchart depicting a method of navigating electrodes of a lead to a target site within a patient using an indicator of the lead.

FIG. 9 is a flow diagram illustrating a method of orienting electrodes of lead 120 at a target site within patient 8 using indicator 114. Although the techniques of FIG. 8 will be described with reference to lead 120 of FIGS. 2A-3, it will be appreciated that the techniques of FIG. 9 may be completed with any of the leads described herein. The flow diagram of FIG. 9 is discussed in conjunction with FIGS. 10A-10E for purposes of clarity only.

Figure 10A:
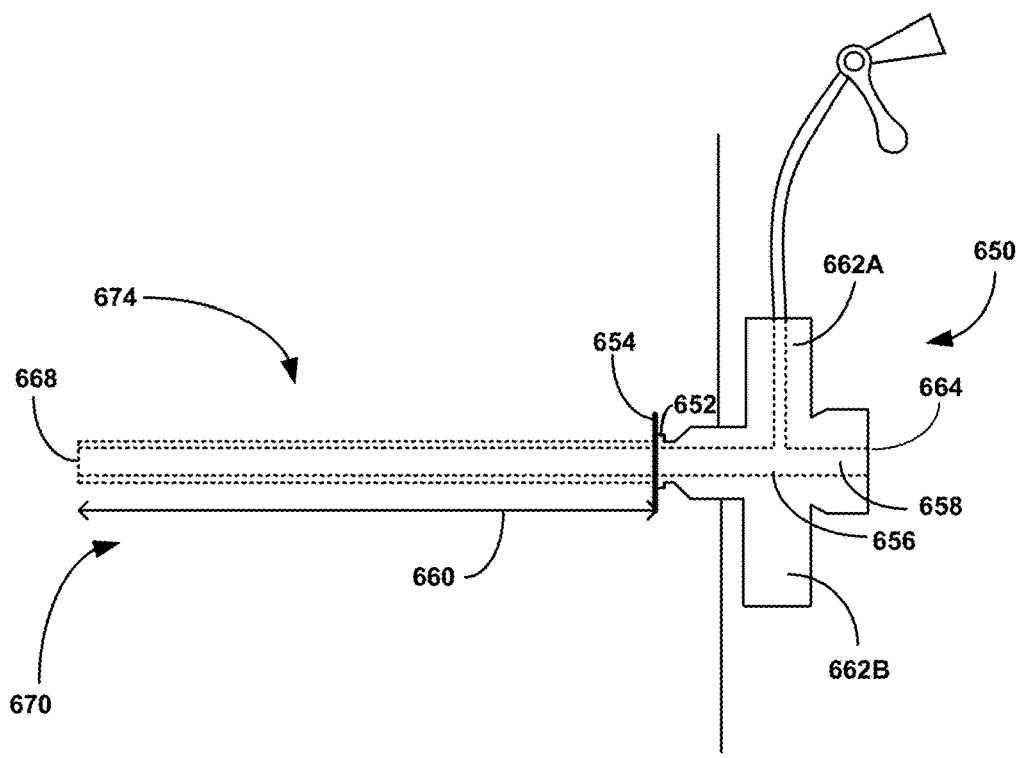
FIGS. 10A and 10B are conceptual and schematic diagrams illustrating perspective views of an example introducer sheath inserted into a patient and the lead of FIG. 2A inserted into the introducer sheath, respectively.

In FIG. 10A, a clinician may insert introducer sheath 650 into patient 8 (640). The clinician may insert introducer sheath 650 into patient 8 through incision 654. Introducer sheath 650 may be inserted into incision 654 using dilation sheath (not depicted). In some examples incision 654 is in the epidermis of patient 8, though in other examples incision 654 may be made in one or more tissues or organs within patient 8. The clinician may insert introducer sheath 650 to predetermined depth 660 into patient 8. In some examples, introducer sheath 650 may define a feature up to which the clinician inserts the introducer sheath 650 to assist in the clinician inserting the introducer sheath the predetermined depth 660. For example, introducer sheath 650 may include a circumferential lip that extends radially outward from an external surface of introducer sheath 650 at the predetermined distance 660 from exit port 668 of introducer sheath 650, such that the clinician inserts distal portion 674 (e.g., the amount of introducer sheath 650 that is distal of this circumferential lip 652 and defines a longitudinal length that is equal to predetermined depth 660) into patient 8 such that circumferential lip 652 contacts surface of incision 654. Alternatively, or additionally, introducer sheath 650 may define one or more physical marks that may indicate the predetermined depth 660 of introducer sheath 650. For example, a distal length of introducer sheath 650 that defines predetermined depth 660 may be colored different than a proximal portion of introducer sheath 650, such that when the differently-colored portion of introducer sheath 650 is inserted then introducer sheath 650 is inserted the predetermined depth 650. For another example, introducer sheath 650 may include one or more visual markers (such as markings that are colored differently or otherwise are visually identifiable from adjacent portions of introducer sheath 650) on an outer surface of introducer sheath 650 that are a distance equal to predetermined depth 660 away from exit port 668, such that inserting introducer sheath 650 up to these markings results in introducer sheath 650 being inserted to predetermined depth 660.

Introducer sheath 650 may define lumen 656 configured to receive lead 120. Lumen 656 may extend between entry port 664 and exit port 668. Introducer sheath 650 may define an orientation region 658, which may be a predetermined discrete portion on an outer surface of introducer sheath 650 to which indicator 114 is configured to be aligned (e.g., such that a clinician may align indicator 114 with orientation region 658 to align distal portion 102 of lead 120). Orientation region 658 may be located adjacent entry port 664 of lumen 656 of introducer sheath 650. In some examples (e.g., such as orientation region 692 on FIGS. 12A-12B), orientation region 658 may be a section of introducer sheath 650 that is visually distinct from adjacent portions of introducer sheath 650. For example, orientation region 658 may be colored differently or may include a radially raised or recessed portion of introducer sheath 650. In other examples (e.g., as depicted in FIGS. 10A-10D) orientation region 658 may be a "top" portion of introducer sheath 650 that is configured to face away from patient 8 and therein face the clinician when introducer sheath 650 is inserted into patient 8.

In some examples, introducer sheath 650 may be a splittable introducer sheath. Introducer sheath 650 may be a splittable sheath as a result of introducer sheath being configured to be split (e.g., by hand) to expose lumen 656 of introducer sheath. For example, a clinician may split introducer sheath 650 by applying a force to both arms 662A, 662B of introducer sheath 650. Introducer sheath 650 may define a weakening element along a longitudinal length of introducer sheath 650 to control such a split. For example, introducer sheath 650 may be thinner and/or include a set of longitudinal perforations along one side of introducer sheath to define a weakened seam that is parallel with the longitudinal axis of introducer sheath 650 along which introducer sheath 650 may be split.

Figure 10B:
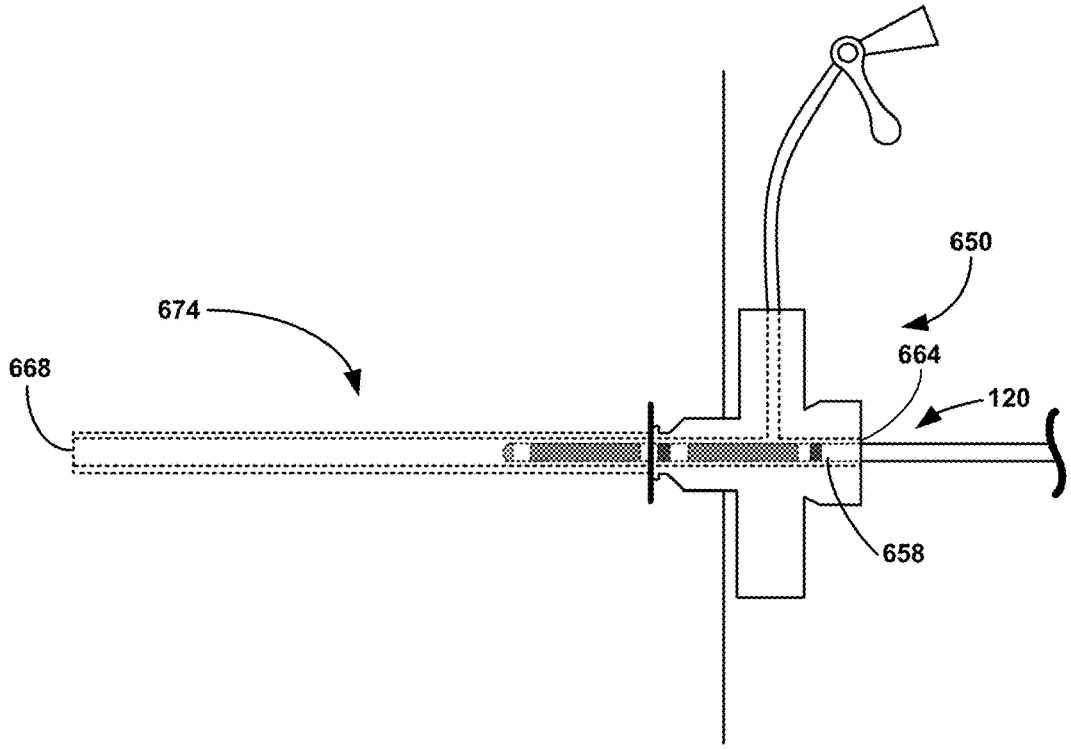

A clinician may select incision 654 site based upon target site 670 to which distal portion 102 of lead 120 is to be navigated and therein provide therapy and/or monitoring. As such, incision 654 may be at a variety of locations depending upon target site 670 as discussed herein. For example, incision 654 may be through skin of patient 8 at a predetermined location approximately 1.5 centimeters below the xiphisternal junction where target site 670 is a substernal location. Incision 654 may have a predetermined distance between itself and target site 670, such that predetermined depth 660 is substantially similar across a plurality of different patients (and therein distal portion 674 is a correct length for that plurality of patients). As a result of the predetermined depth 660 being substantially similar, upon distal portion 674 being inserted at incision 654, distal portion 102 of lead 120 may reliably and repeatably be navigated to target site 670 upon being deployed from exit port 668. In response to properly inserted introducer sheath 650 into patient 8, a clinician may insert lead 120 into entry port 664 of introducer sheath 650 (642) as depicted in FIG. 10B.

Figure 10C:
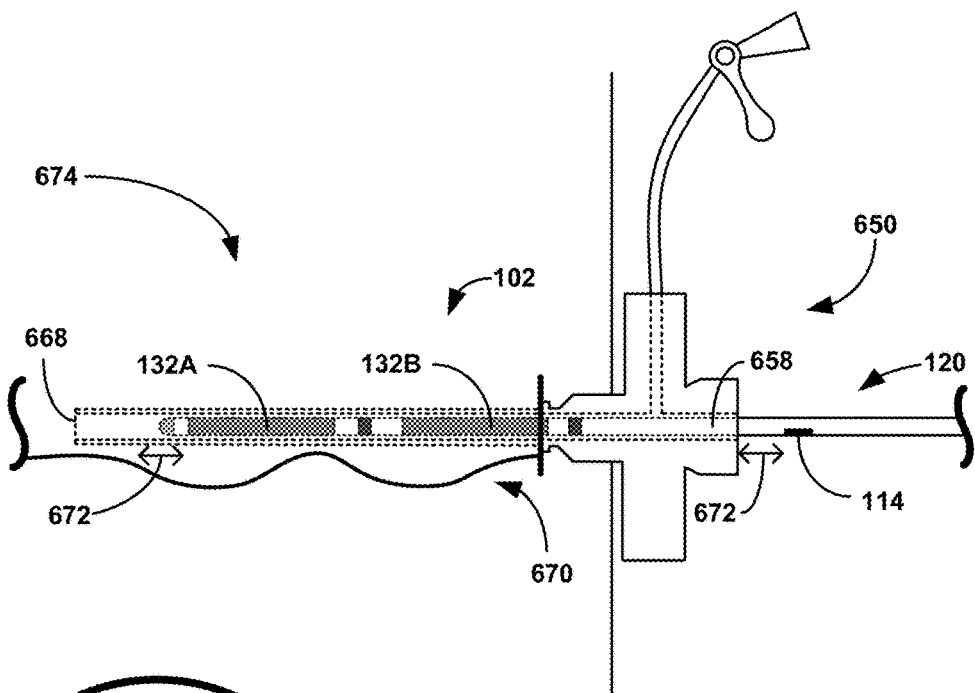
FIGS. 10C and 10D are conceptual and schematic diagrams illustrating perspective views of the lead of FIG. 2A navigating the distal portion to a target site and being oriented properly at the target site, respectively.

In FIG. 10C, a clinician may navigate distal portion 102 of lead 120 to target site 670 (644). As discussed herein, target site 670 may be at a plurality of locations, such as at a location alongside heart 18. The target site 670 may include a set of locations at which it is efficacious for distal portion 102 of lead 120 to occupy upon being deployed from introducer sheath 650. For example, as depicted, target site 670 includes a serpentine shape which might be efficacious for the reasons described herein. Put differently, target site 670 as depicted in FIGS. 10C and 10D may include an axis which lead 120 is configured to occupy upon deployment.

As the clinician navigates the distal portion 102 toward target site 670, the clinician may use indicator 114 to orient distal portion 102 (646). For example, as depicted in FIG. 10C, a clinician may identify that indicator 114 is longitudinal length 672 away from orientation region 658, which may correlate to longitudinal length 672 electrode 132A is from first curve of target site 670. Similarly, the clinician may detect that indicator 114 is not radially centered on orientation region 658 but is instead rotated 90° away from orientation region 658 (e.g., such that if deployed in its current radial alignment, distal portion 102 of lead 120 may define serpentine shape 112 as curving into the page rather than aligning with shape of target site 670). Given the axial and rotation stiffness of lead 120 as discussed herein, distal portion 102 of lead 120 may also be rotated approximately 90° away from target site 670.

Figure 10E:
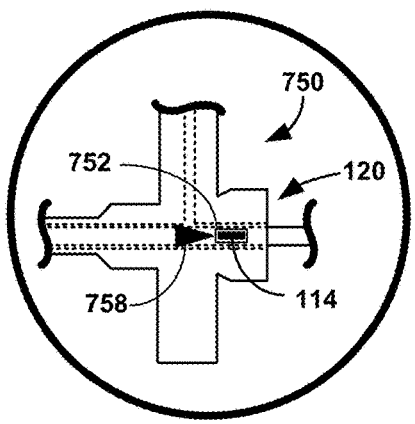
FIG. 10E is a conceptual and schematic diagram illustrating the lead of FIG. 2A being aligned using an example introducer sheath that includes an alignment window.
Figure 10D:
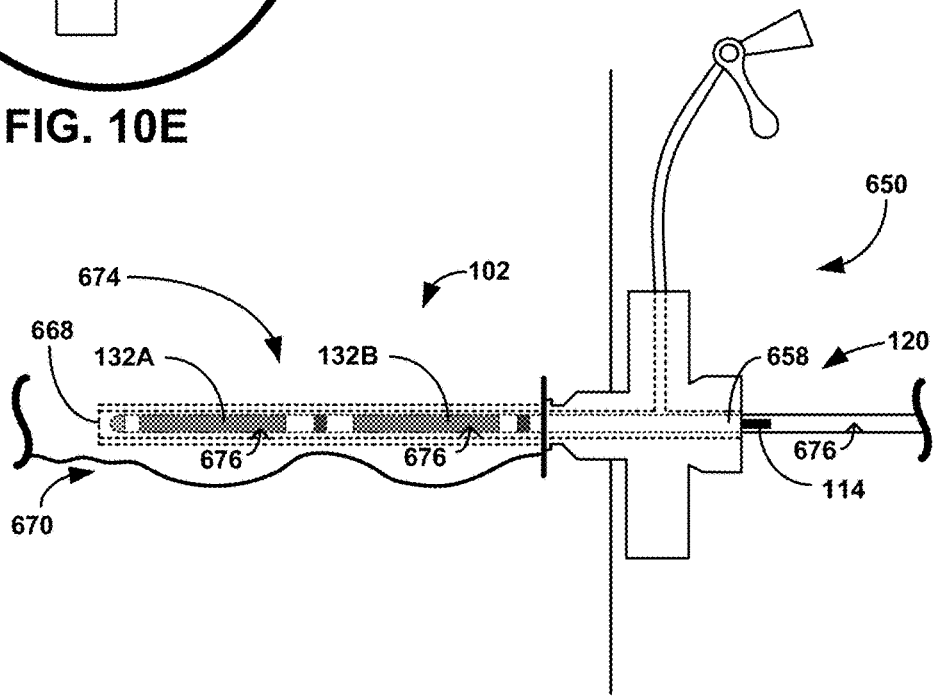

In FIG. 10D, the clinician has rotated and advanced lead 120 to align orientation region 658 and indicator 114. As depicted, electrode 132 has been rotated per rotation 676 and advanced along with indicator 114, such that distal portion 102 of lead 120 is properly oriented adjacent target site 670. For example, the distal end of lead 120 may be longitudinally aligned with the distal end of introducer sheath 650, and the radially orientation of lead 120 may provide for the configuration shown in FIG. 1A, e.g., with regard to the peaks and valleys of lead 120 when in an unconstrained state. As a result of using external indicator 114 that is visible without imaging tools, a clinician may navigate distal portion 102 of lead 120 to target site 670 of patient 8 without using fluoroscopy or the like, therein reducing an amount of radiation exposure of patient 8. Further, indicator 114 may enable to proper longitudinal and radial orientation of distal portion 102 of lead 120 at target sites 670 where fluoroscopy is difficult or impossible (e.g., due to nearby metallic implants or medical situations or the like).

In some examples, an introducer sheath may include a window through which an indicator of a lead may be aligned to verify that a distal portion of a lead is properly oriented at/adjacent a target site. For example, FIG. 10E depicts a conceptual and schematic diagram illustrating introducer sheath 750 that includes alignment window 752. In examples where introducer sheath 750 includes alignment window 752 or the like, a clinician may insert introducer sheath 750 such that alignment window 752 faces the clinician (e.g., faces away from patient 8) upon insertion.

Introducer sheath 750 may be substantially similar to introducer sheath 650 with the exception of any differences described herein. In some examples, alignment window 752 may be a hole or bore that extends radially through to a lumen of introducer sheath 750, while in other examples alignment window 752 may include a relatively transparent region of introducer sheath 750. Introducer sheath 750 may include alignment window 752 at a predetermined axial and radial location such that, when indicator 114 of lead 120 is within alignment window 752 and introducer sheath 750 is inserted into patient 8 at a predetermined depth, distal portion 102 is properly longitudinally and radially oriented at target site 670. As discussed herein, introducer sheath 750 may include one or more visual markings that indicate when introducer sheath 750 is inserted to the predetermined depth. Introducer sheath 750 may be configured such that, when introducer sheath 750 is inserted to the predetermined depth within an adult patient and lead 120 is inserted into introducer sheath 750 and patient 8 such that indicator 114 is aligned with alignment window 752, distal portion 102 of lead 120 may be properly longitudinally and radially orientated at the target site for, e.g., 95% of patients. Including alignment window 752 within introducer sheath 750 may improve an ability of a clinician to longitudinally and radially orient distal portion 102 of lead 120 at target site 670 within patient 8.

In some examples, a clinician may split introducer sheath 650 following the successful insertion of lead 120. For example, FIGS. 11A and 11B depict conceptual and schematic diagrams of lead 120 and introducer sheath 650 inserted to a substernal location and of introducer sheath 650 being split and withdrawn, respectively. As depicted in FIG. 11A, as initially navigated a target site below sternum 24, lead 120 may be received by introducer sheath 650 in constrained state 101. In some examples, as a result of constrained state 101 straightening curved sections 110 of lead 120, distal portion 102 of lead 120 may extend somewhat past a target site below sternum 24. As depicted in FIG. 11B, introducer sheath 650 may be split and retracted/withdrawn proximally. As introducer sheath 650 retracts, distal portion 120 of lead may extend out of exit port 668 of introducer sheath 650 to assume unconstrained state 100. As depicted, distal portion 102 may retract proximally somewhat due to curved sections 110 defining serpentine shape 112 as lead 120 transitions from constrained state 101 to unconstrained state.

Figure 12A:
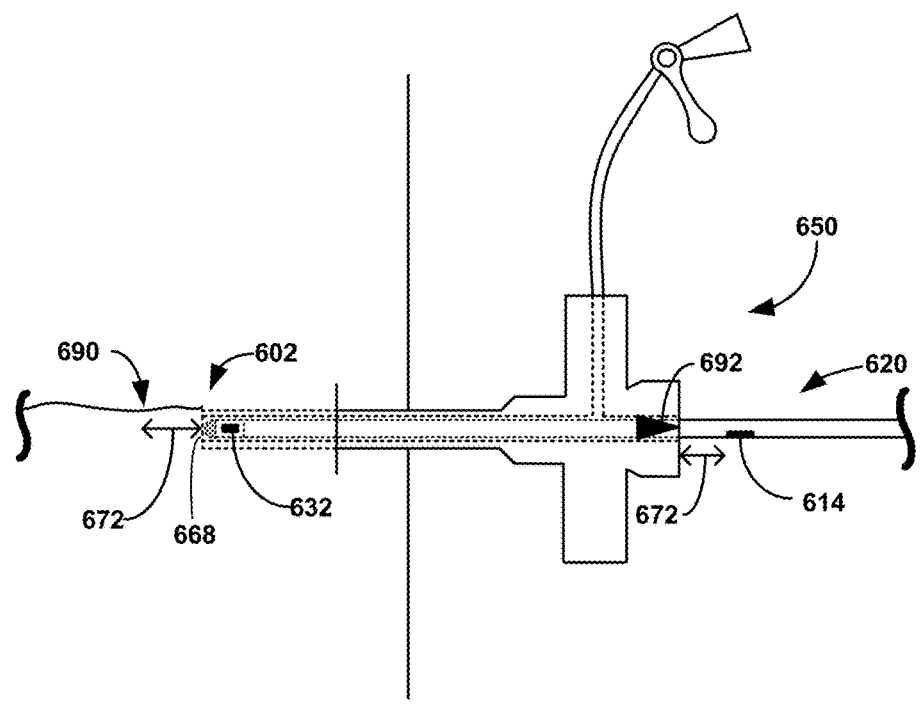
FIGS. 12A and 12B are conceptual and schematic diagrams illustrating perspective views of the lead of FIG. 8B navigating the distal portion to a target site and being oriented properly at the target site, respectively.
Figure 12B:
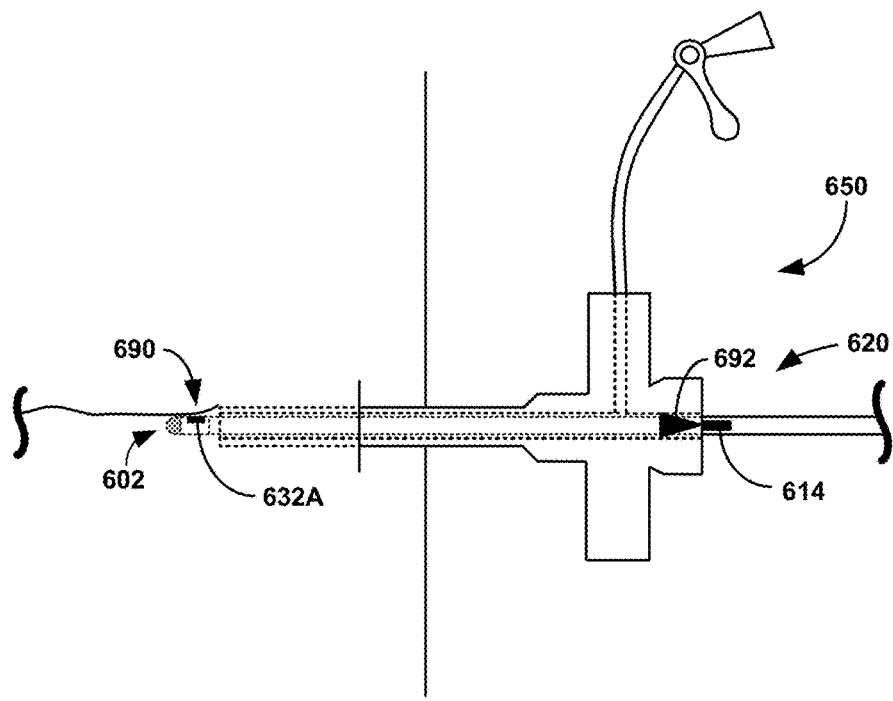

In some examples, leads may be navigated to target sites that are somewhat distal of an exit port of introducer sheath using indicator. For example, FIGS. 12A and 12B depict conceptual and schematic diagrams of lead 620 being navigated to and oriented at target site 690 that is distal to exit port 668 of introducer sheath, respectively. Although the FIGS. 12A and 12B will be described with reference to lead 620 of FIGS. 8A-8C, it will be appreciated that aspects of the discussion below may apply to other aspects of this disclosure. In FIG. 12A, a clinician may navigate distal portion 102 of lead 120 to target site 690. As discussed herein, target site 690 may be at a plurality of locations, such as at a location alongside heart 18, or a location within a brain of a patient for DBS, or a location adjacent a spinal cord for SCS. The target site 690 may include a location at which it is efficacious for electrode 632 to directly press up against tissue of target site 690. As depicted, target site 690 may be distal of exit port 668 of introducer sheath 650, though in other examples target site 690 may be further from exit port 668 (e.g., such that lead 620 may navigate intravenous system of patient 8 before arriving at target site 690).

As the clinician navigates the distal portion 602 toward target site 670, the clinician may use indicator 614 to orient electrode 632 against target site 690. For example, as depicted in FIG. 12A, a clinician may identify that indicator 614 is longitudinal length 672 away from orientation region 692, which may correlate to longitudinal length 672 electrode 632 is from target site 690. Similarly, the clinician may detect that indicator 614 is not radially centered on orientation region 692 but is instead rotated 90° away from orientation region 692. Given the axial and rotation stiffness of lead 620 as discussed herein, electrode 632 may also be rotated approximately 90° away from target site 690.

In FIG. 12B, the clinician has rotated and advanced lead 620 to align orientation region 692 and indicator 614. As depicted, electrode 632 has been rotated and advanced along with indicator 614, such that electrode 632 is properly navigated to target site 690. As a result of using external indicator 614 that is visible without imaging tools, a clinician may navigate electrodes 632 and the like to target site 690 of patient 8 without using fluoroscopy or the like, therein reducing an amount of radiation exposure of patient 8. Further, indicator 614 may enable to proper longitudinal and radial orientation of electrode 632 at target sites 690 where fluoroscopy is difficult or impossible (e.g., due to nearby metallic implants or medical situations or the like).

Figure 13:
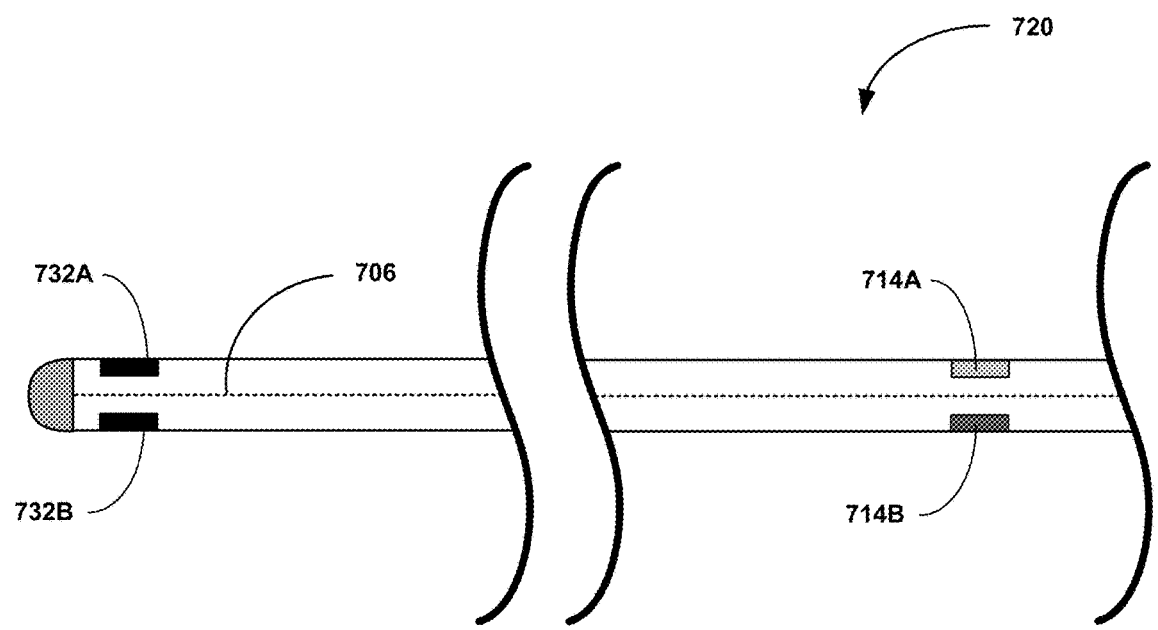
FIG. 13 is a conceptual and schematic diagram illustrating a plurality of example visible indicators of a lead that correlate to a plurality of electrodes of the lead.

In some examples, leads may include a plurality of indicators, whether working in conjunction to indicate an orientation of a single element or each indicating an orientation of a different element. For example, FIG. 13 is a conceptual and schematic diagram of example lead 720 that that includes a plurality of indicators 714A, 714B (collectively, "indicators 714") that indicate an orientation of respective electrodes 732A, 732B (collectively, "electrodes 732"). Lead 720 may be substantially to lead 20, 120, 220, 320, 420, 520, 620, and indicators 714 may be substantially similar to indicators 14, 114, 214, 314, 414, 514, 614 with the exception of any differences described herein. Similarly, electrodes 732 may be substantially similar to any of electrodes 32, 34, 132, 632, with the exception of any differences described herein. Electrodes 732 are depicted and discussed as segmented electrodes (similar to electrodes 632) herein for purposes of discussion, though in other examples electrodes 732 may be other shapes or types or arranged differently than in FIG. 13.

As depicted in FIG. 13, lead 720 includes two indicators 714. Each indicator 714 may indicate a relative longitudinal and radial orientation of one of electrodes 732. For example, indicator 714A may indicate a longitudinal and radial orientation of electrode 732A, and indicator 714B may indicate a longitudinal and radial orientation of electrode 732B. In this example, both electrodes 732 and indicators 714 may be radially arranged 180° apart around longitudinal axis 706 of lead 720, though in other examples (e.g., examples where there are more than two electrodes 732 and therein more than two indicators 714) electrodes 732 and indicators 714 may be radially arranged in other manners. In examples where electrodes 732 of lead 720 are at different longitudinal positions, indicators 714 may similarly be at different positions. Indicators 714 may be visually distinct from each other so that a clinician may know which electrode 732 a respective indicator 714 is indicating an orientation of. Indicators 714 may be visually distinct in any of the manners described herein (e.g., such as visually distinct through one or more constructions or techniques described and depicted in FIGS. 4-7), such as colored differently as depicted in FIG. 13.

Figure 14:
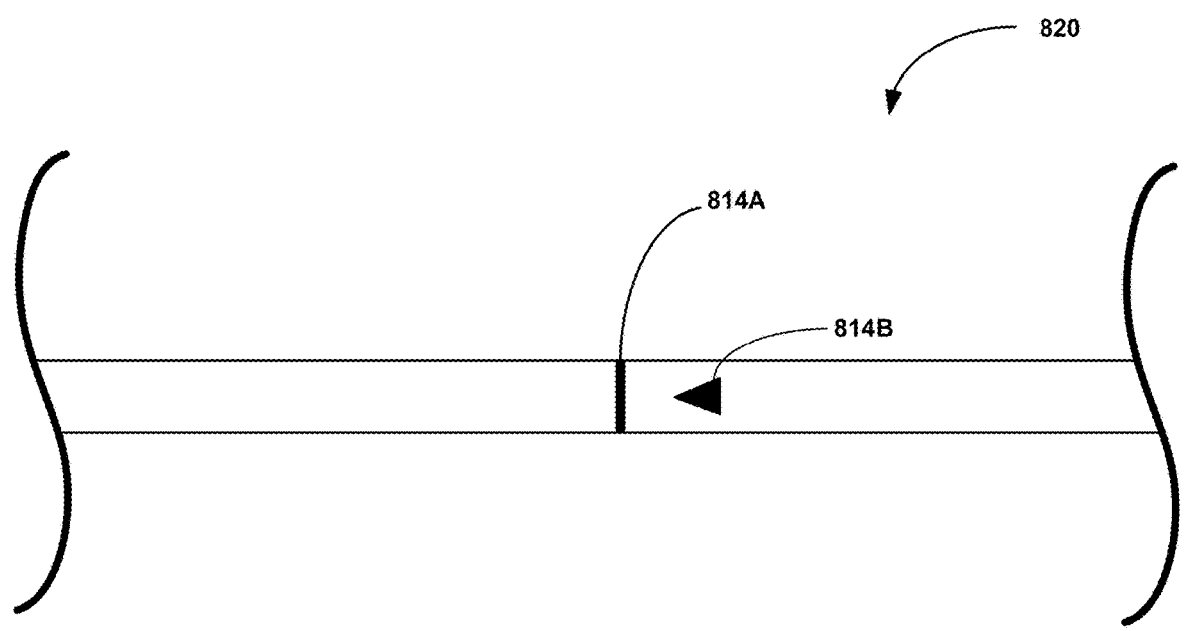
FIG. 14 is a conceptual and schematic diagram illustrating a first visible indicator of a lead that indicates a longitudinal orientation and a second visible indicator of the lead that indicates a radial orientation of electrodes of the lead.

For another examples of a lead that includes a plurality of indicators, FIG. 14 is a conceptual and schematic diagram of example lead 820 that that includes a plurality of indicators 814A, 814B (collectively, "indicators 814") that indicate an orientation of a distal portion of lead 720. Lead 820 may be substantially to lead 20, 120, 220, 320, 420, 520, 620, 720, and indicators 814 may be substantially similar to indicators 14, 114, 214, 314, 414, 514, 614, 714 with the exception of any differences described herein.

As depicted in FIG. 14, lead 820 includes two indicators 814. One indicator 814A may indicate a longitudinal orientation of a distal portion of lead 820, and one indicator 814B may indicate a radial orientation of the distal portion of lead 820. Indicators 814 may be visually and physical distinct from each other. For example, indicator 814A may be a band of a solid color on lead 820 that runs around a full perimeter of lead 820, while indicator 814B is a shape (such as the triangle as depicted) upon only one side of lead 820. When implanting lead 820 into an introducer sheath, a clinician may insert lead 820 up to longitudinal indicator 814A (to correctly longitudinally orient the distal portion of lead 820 at the target site), after which the clinician may rotate (as necessary) lead 820 to properly orient radial indicator 814B (to correctly radially orient the distal portion of lead 820 at the target site) while holding the lead 820 at the same longitudinal location. In this way, two indicators 814 that are each visually distinct from each other on lead 820 may, in conjunction, indicate the longitudinal and radial orientation of a single element or portion of lead 820.

This disclosure is primary directed to medical delivery devices that include one or more visible indicators that indicate a longitudinal and radial orientation of electrodes of a lead to assist in the delivery of the electrodes to a target site near a heart of a patient. However, one or more aspects of this disclosure may also be applicable to other examples, such as using the indicators as discussed herein to navigate a lead to another location near a spine of a patient or within a cranium of a patient. In one or more of these examples, the lead may navigate through the patient before arriving at the target site in one or more ways, such that the lead may be shaped differently to better navigate these areas of the body. Further, in other examples the indicator may be at other relative distances along the lead and/or other radial spots along the lead to indicate the position for the different applications. Other applications for aspects of this disclosure would also be understood by one of ordinary skill in the art.

Various examples have been described. These and other examples are within the scope of the following claims.

The invention claimed is:

1. An implantable medical lead comprising:
   a distal portion that defines a serpentine shape and extends proximally from a distal tip of the implantable medical lead;
   a proximal portion configured to be coupled to an implantable medical device;
   at least one visible indicator located between the distal portion and the proximal portion at a discrete radial position and a discrete longitudinal position between 18 and 25 centimeters from the distal tip along a longitudinal axis of the implantable medical lead, wherein the at least one visible indicator is configured to indicate a radial orientation of the distal portion of the implantable medical lead and indicate a depth of the distal portion of the implantable medical lead in a patient when the distal portion is adjacent a target site in the patient while the at least one visible indicator is external to the patient;
   a first pacing and/or sensing electrode that defines a proximal edge between 10 and 12 centimeters distal of the visible indicator along the longitudinal axis;
   a first defibrillation electrode that defines a proximal edge between 11 and 13 centimeters distal of the at least one visible indicator along the longitudinal axis and is configured to curve toward a right side of a heart of the patient upon implantation;
   a second pacing and/or sensing electrode that defines a proximal edge between 14.5 and 16.5 centimeters distal of the at least one visible indicator along the longitudinal axis; and
   a second defibrillation electrode that defines a proximal edge between 15 and 17 centimeters distal of the at least one visible indicator along the longitudinal axis and is configured to curve toward the right side of the heart of the patient upon implantation; and
   an introducer sheath including a distal portion configured to be inserted into the patient to a targeted depth and an entry port at a proximal portion of the introducer sheath, wherein the distal portion of the implantable medical lead is configured to be inserted into the entry port of the introducer sheath and moved towards the distal portion of the introducer sheath, and wherein the at least one visible indicator is configured to indicate the radial orientation of the distal portion of the implantable medical lead within the introducer sheath and indicate the depth of the distal portion of the implantable medical lead within the introducer sheath; wherein the proximal portion of the introducer sheath includes a window adjacent the entry port of the introducer sheath and configured to be located outside the patient when the distal portion of the introducer sheath is at the targeted depth.

2. The implantable medical lead of claim 1, wherein the implantable medical lead includes an anchoring portion of the implantable medical lead that defines a distal end of the anchoring portion between 1 and 2 centimeters proximal of the first pacing and/or sensing electrode and extends proximally between 9 and 12 centimeters from the distal end, wherein an outer surface of the anchoring portion defines an interlocking interface; and
   an anchoring sleeve that is slideable over the anchoring portion and is configured to interlock with the interlocking interface in response to the anchoring sleeve being anchored to the patient.

3. The implantable medical lead of claim 1, wherein the at least one visual indicator is further configured to indicate a depth of one or more of the first pacing and/or sensing electrode, the first defibrillation electrode, the second pacing and/or sensing electrode, and the second defibrillation electrode of the implantable medical lead within a patient.

4. The implantable medical lead of claim 1, wherein the implantable medical lead is between 45 and 70 centimeters long along the longitudinal axis.

5. The implantable medical lead of claim 1, wherein the distal portion includes:
   a straight section that is configured to extend substantially straight in a proximal direction from the first pacing and/or sensing electrode for between 1 and 2 centimeters; and
   a curved section that immediately proximal the straight section and is configured to curve toward a subclavical implant site of the implantable medical device.

6. The implantable medical lead of claim 5, wherein an anchoring portion is immediately proximal to the straight section.

7. The implantable medical lead of claim 1, wherein the at least one visible indicator is visible to the naked eye.

8. The implantable medical lead of claim 1, wherein the at least one visible indicator includes a single visual indicator on the implantable medical lead at the discrete longitudinal position and the discrete radial position between the distal portion and the proximal portion.

9. The implantable medical lead of claim 1, wherein the at least one visible indicator includes a first visible indicator at the discrete longitudinal position on the implantable medical lead and a second visible indicator at the discrete radial position.

10. The implantable medical lead of claim 1, wherein the at least one visible indicator is visible without the use of fluoroscopy.

11. An implantable medical device system comprising:
an implantable medical lead comprising:
a distal portion that defines a serpentine shape and extends proximally from a distal tip of the implantable medical lead;
a proximal portion configured to be coupled to an implantable medical device;
at least one visible indicator located between the distal portion and the proximal portion at a discrete radial position and a discrete longitudinal position between 18 and 25 centimeters from the distal tip along a longitudinal axis of the implantable medical lead, wherein the at least one visible indicator is configured to indicate a radial orientation of the distal portion of the implantable medical lead and indicate a depth of the distal portion of the implantable medical lead in a patient when the distal portion is adjacent a target site in the patient while the at least one visible indicator is external to the patient;
a first pacing and/or sensing electrode that defines a proximal edge between 10 and 12 centimeters distal of the visible indicator along the longitudinal axis;
a first defibrillation electrode that defines a proximal edge between 11 and 13 centimeters distal of the at least one visible indicator along the longitudinal axis and is configured to curve toward a right side of a heart of the patient upon implantation;
a second pacing and/or sensing electrode that defines a proximal edge between 14.5 and 16.5 centimeters distal of the at least one visible indicator along the longitudinal axis; and
a second defibrillation electrode that defines a proximal edge between 15 and 17 centimeters distal of the at least one visible indicator along the longitudinal axis and is configured to curve toward the right side of the heart of the patient upon implantation; and
an implantable medical device configured to at least one of generate electrical stimulation or monitor sensed electrical signals of the patient when implanted within the patient and coupled to the proximal portion of the implantable medical lead; and
an introducer sheath including a distal portion configured to be inserted into the patient to a targeted depth and an entry port at a proximal portion of the introducer sheath, wherein the distal portion of the implantable medical lead is configured to be inserted into the entry port of the introducer sheath and moved towards the distal portion of the introducer sheath, and wherein the at least one visible indicator is configured to indicate the radial orientation of the distal portion of the implantable medical lead within the introducer sheath and indicate the depth of the distal portion of the implantable medical lead within the introducer sheath; wherein the proximal portion of the introducer sheath includes a window adjacent the entry port of the introducer sheath and configured to be located outside the patient when the distal portion of the introducer sheath is at the targeted depth.

12. The implantable medical device system of claim 11, wherein a length of the introducer sheath and a location of the at least one visible indicator on the implantable medical lead are such that, when a distal end of the implantable medical lead is at a position near a distal end of the introducer sheath and the distal portion of the introducer sheath is at the targeted depth, the at least one visible indicator is located outside the patient, is nearer the entry port of the introducer sheath than the distal end of the introducer sheath, and is visible without the use of fluoroscopy.

13. The implantable medical device system of claim 11, wherein the distal portion of the implantable medical lead is configured to be received by the introducer sheath in a constrained state that defines a relatively straight shape, wherein the distal portion of the implantable medical lead is configured to define the serpentine shape when in an unconstrained state following deployment of the distal portion of the implantable medical lead.

14. The implantable medical device system of claim 11, wherein the introducer sheath is a splittable introducer sheath.

15. The implantable medical device system of claim 11, wherein a length of the introducer sheath and a location of the at least one visual indicator on the implantable medical lead are such that, when a distal end of the implantable medical lead is at a position near the distal end of the introducer sheath and the distal portion of the introducer sheath is at the targeted depth, the at least one visual indicator is configured to be viewable through the window in the introducer sheath to indicate the depth of the distal portion of the implantable medical lead within the introducer sheath.

16. The implantable medical device system of claim 11, wherein the at least one visible indicator is visible to the naked eye without the use of fluoroscopy.

17. The implantable medical device system of claim 11, wherein the implantable medical lead includes an anchoring portion of the implantable medical lead that defines a distal end of the anchoring portion between 1 and 2 centimeters proximal of the first pacing and/or sensing electrode and extends proximally between 9 and 12 centimeters from the distal end, wherein an outer surface of the anchoring portion defines an interlocking interface; and
an anchoring sleeve that is slideable over the anchoring portion and is configured to interlock with the interlocking interface in response to the anchoring sleeve being anchored to the patient.

18. The implantable medical device system of claim 11, wherein the at least one visual indicator is further configured to indicate a depth of one or more of the first pacing and/or sensing electrode, the first defibrillation electrode, the second pacing and/or sensing electrode, and the second defibrillation electrode of the implantable medical lead within a patient.

* * * * *